United States Patent
Dobson et al.

(10) Patent No.: US 11,901,073 B2
(45) Date of Patent: Feb. 13, 2024

(54) ONLINE SOCIAL HEALTH NETWORK

(71) Applicant: RYKOV LLC, Dacula, GA (US)

(72) Inventors: Melissa K Dobson, Painted Post, NY (US); Owen N. Dobson, Dacula, GA (US); Austin S. Dobson, Dacula, GA (US)

(73) Assignee: RYKOV LLC, Dacula, GA (US)

( * ) Notice: Subject to any disclaimer, the term of this patent is extended or adjusted under 35 U.S.C. 154(b) by 129 days.

(21) Appl. No.: 16/634,896

(22) PCT Filed: Jun. 21, 2019

(86) PCT No.: PCT/US2019/038540
§ 371 (c)(1),
(2) Date: Jan. 29, 2020

(87) PCT Pub. No.: WO2020/018233
PCT Pub. Date: Jan. 23, 2020

(65) Prior Publication Data
US 2020/0234825 A1      Jul. 23, 2020

Related U.S. Application Data

(60) Provisional application No. 62/661,163, filed on Apr. 23, 2018.

(51) Int. Cl.
*G16H 10/60* (2018.01)
*G16H 40/20* (2018.01)
*G16H 50/20* (2018.01)

(52) U.S. Cl.
CPC .............. *G16H 50/20* (2018.01); *G16H 10/60* (2018.01); *G16H 40/20* (2018.01)

(58) Field of Classification Search
CPC ......... G16H 40/20; G16H 10/60; G16H 50/20
See application file for complete search history.

(56) References Cited

U.S. PATENT DOCUMENTS

2012/0129139 A1    5/2012   Partovi
2012/0284045 A1    11/2012  Hicks et al.
(Continued)

OTHER PUBLICATIONS

International Preliminary Report on Patentability for corresponding PCT Application No. PCT/US2019/038540 dated Feb. 27, 2020, 7 pages.
(Continued)

*Primary Examiner* — Michael Tomaszewski
*Assistant Examiner* — Mohmad Muqueeth
(74) *Attorney, Agent, or Firm* — Hoffman Warnick LLC

(57) ABSTRACT

The system disclosed allows a user to specify an illness, disease, or health condition, mental or physical or otherwise, and interconnect with other users having similar diagnoses, symptoms, conditions, complications, treatments, or otherwise. The patient user may be connected to a caregiver who links into the system to connect with other caregivers as well. The social network is a health web designed to interconnect patients, friends, families, doctors or others who seek personalized medical information pertaining to the experiences of others. The system allows an interconnection of patients who want to correspond as to symptoms and treatments, and/or for medical professionals who seek to expand their global knowledge base as to collegial networks for diagnosis, treatment, and real-time evaluation. The social network provides a global interface, connected via mobile device, remotely for medical treatment globally, from the latest innovations in medicine to the remote locations of the world.

21 Claims, 13 Drawing Sheets

(56) References Cited

U.S. PATENT DOCUMENTS

| | | |
|---|---|---|
| 2015/0161349 A1 | 6/2015 | Rodriguez |
| 2015/0216413 A1 | 8/2015 | Soyao et al. |
| 2015/0261917 A1* | 9/2015 | Smith ................. G06F 21/6263 705/3 |
| 2015/0363553 A1 | 12/2015 | Rustgi et al. |
| 2016/0042133 A1* | 2/2016 | Sidel ...................... G16H 50/20 705/51 |
| 2018/0082024 A1 | 3/2018 | Curbera et al. |
| 2020/0273570 A1 | 8/2020 | Subramanian et al. |

OTHER PUBLICATIONS

International Search Report and Written Opinion for corresponding PCT Application No. PCT/US2019/038540 dated Mar. 25, 2020, 8 pages.

* cited by examiner

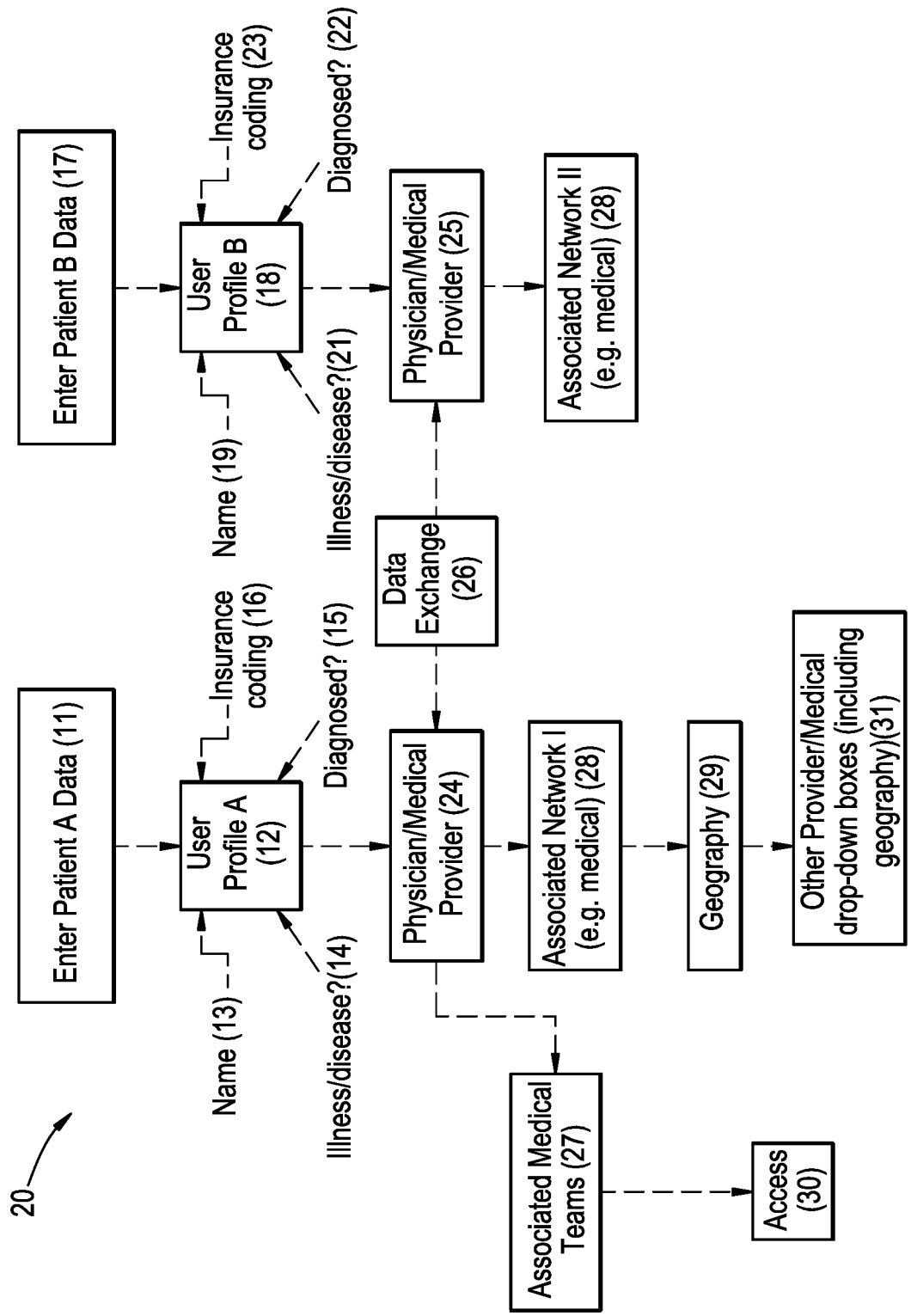

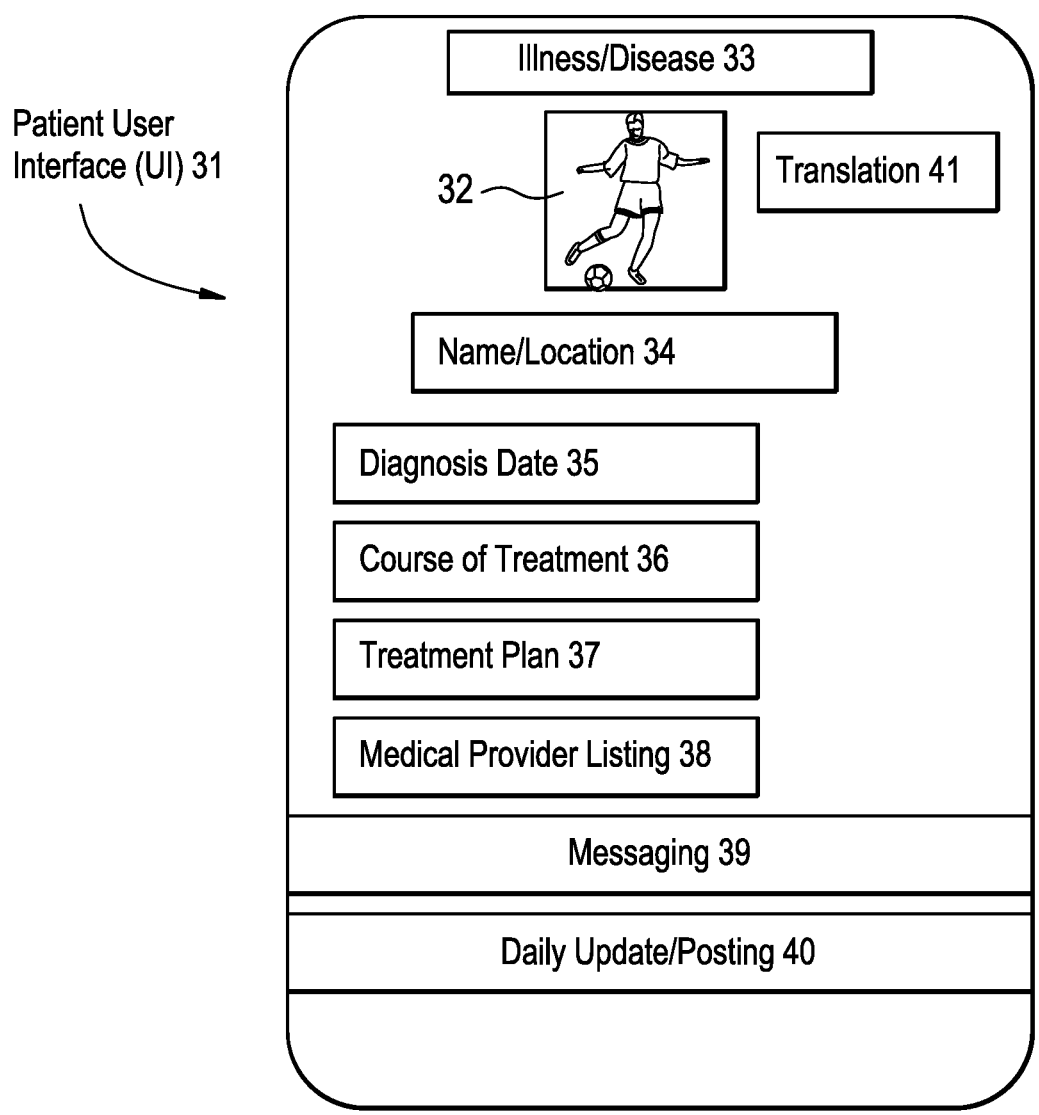

FIG. 8
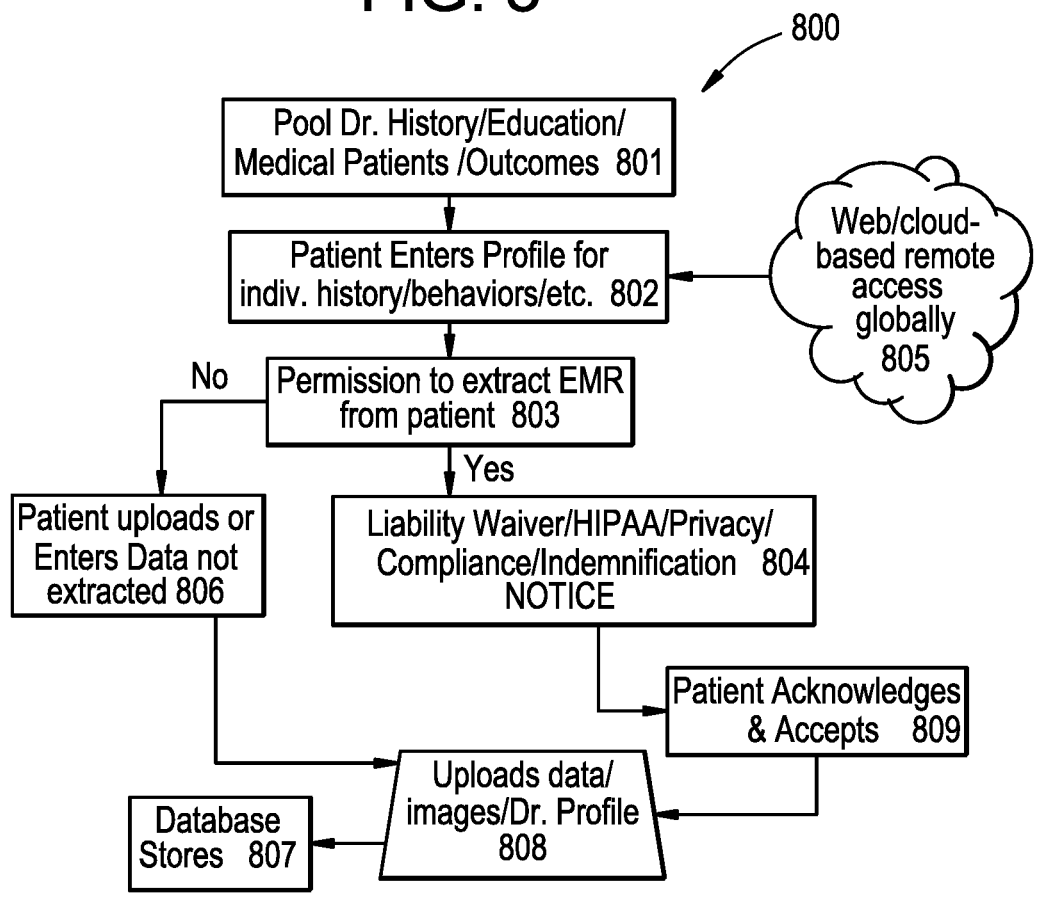
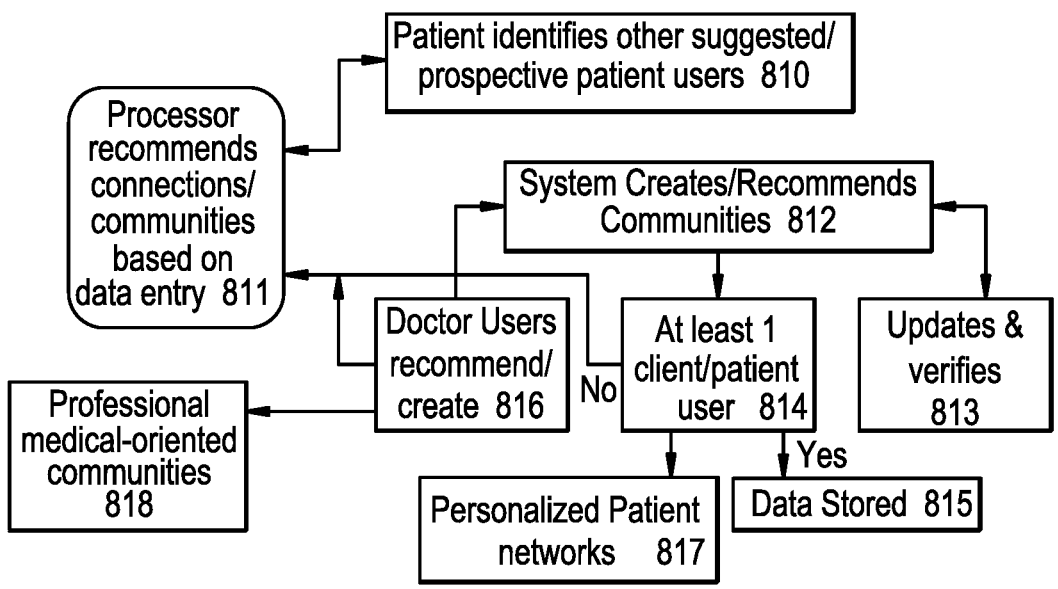

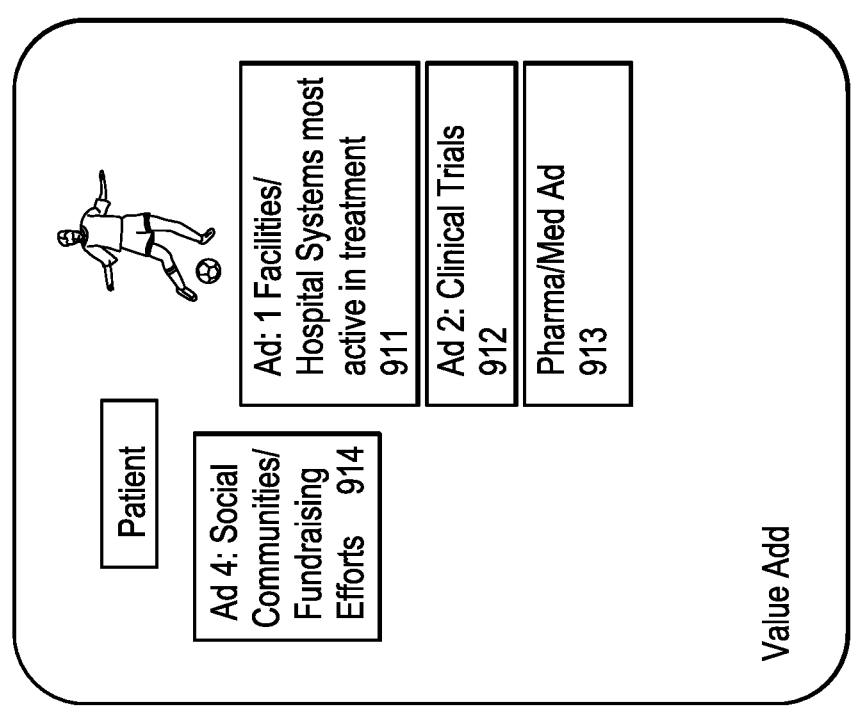
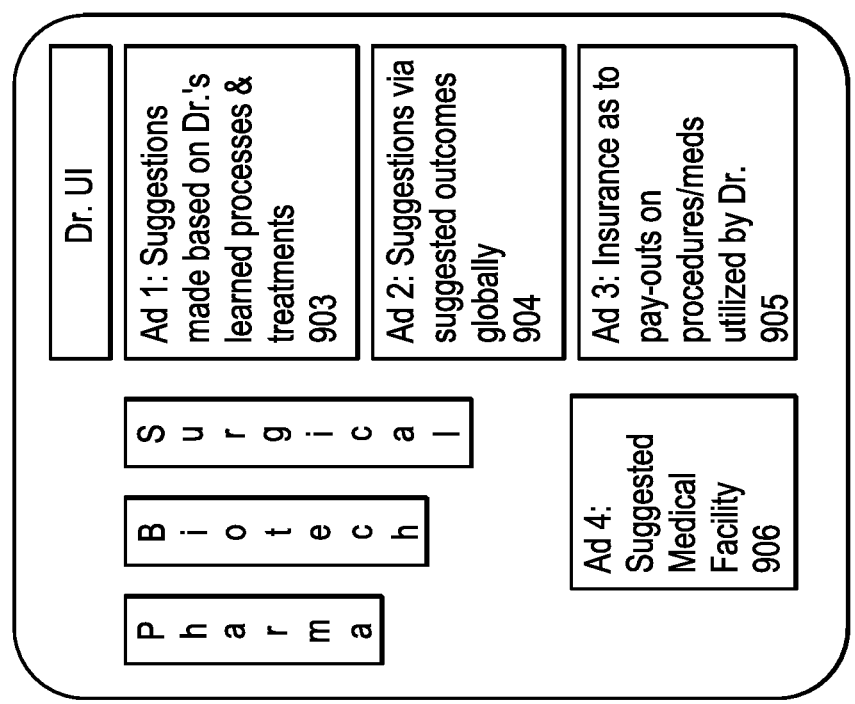

ONLINE SOCIAL HEALTH NETWORK

PRIORITY CLAIM

The present application claims priority to U.S. Nonprovisional application Ser. No. 16/392,623, filed Apr. 24, 2019 (with a right to restore priority), titled Online Social Health Network, which claims priority to U.S. Nonprovisional application Ser. No. 16/501,361, filed Apr. 24, 2019 (with a right to restore priority), titled Online Social Health Network, and which further claims priority to Provisional application Ser. No. 62/661,163, filed Apr. 23, 2018, titled Online Social Health Network.

FIELD OF THE INVENTION

The present invention relates generally to interconnecting via cloud computing, and more particularly, to a system and method for social networking within the patient community and among medical providers globally.

BACKGROUND OF THE INVENTION

Current social networks allow users to interface based on common daily interactions such as exchanging photos of food, to the latest hairstyle, children's videos, and social event planning. Such social networks such as Twitter, Facebook, Tumblr, Instagram, WhatsApp, SnapChat, among others, fail, however, to have a professional interface that extends beyond common social interactions. Even dating apps such as Match, Bumble, eHarmony, and numerous others available fail to interconnect persons beyond identified personal interests and desires.

Social network services typically consist of online communities of individuals or groups of individuals who share a common background, attributes, interests and/or activities, and who are interested in meeting and/or interacting with other individuals in the network. Most social network services are web-based and provide a variety of ways for users to interact, such as via email, instant messaging, posting blogs, and posting comments on each other's social network profile pages. A number of social network services have developed solutions to accommodate users participating in social networks through use of wireless devices, and other portable electronic devices.

Whether for dating, friendship, activities, deal-making, or reuniting, conventional social networking solutions, such as online social networks, typically require a user who wants to find other members that share similar interests to designate the specific attributes sought at the time the user wants to find these members. It is often difficult to find users with desired qualities because conventional social networking solutions typically have many users, and entering desired attributes often returns too many potential matches. Searching for other members that a user would find of interest oftentimes requires sorting through the profiles and data of many other members and/or performing multiple searches to find individuals of interest. Users of many conventional social networks may also search for individuals that one may have interest in by scanning though the profiles and data of users associated with already-known members. In some instances, meeting individuals who have an established relationship with an already-known individual may require a user to request permission from a user's already-known contact, the person of interest, or both. This results in a delay for the user before the user can meet the person of interest as well as additional user effort. Further, although a user may find another member in a social network desirable and may want to interact with that individual, it is often difficult to determine if the user himself or herself has attributes that the other individual is seeking.

Meanwhile, currently existing health programs, legalities of government, and community systems interfere with connecting resources for individual patients, his/her family and friends and the associated medical providers. Even internal hospital and medical systems, and the software utilized by medical providers, fail to interconnect medical professionals across the globe, or even within a community or the same city. Patient information remains situated within encrypted servers to protect patient data, and respectfully protect privacy via regulatory controls. The systems lack a consistent language or synchrony of software across medical servers, restrict access, and/or do not provide sharing capabilities among patients. Patient portals or any internal medical information remains locked in private accounts.

In addition, medical providers connect through medical associations, annual continuing medical education activities, fundraising, among other in-person servicing, but rely solely on word of mouth and attendance at events to expand knowledge capabilities and interconnections. Even online resources are just that online, without personalized access to patients or medical providers outside their individualized education or professional associations.

The unmet needs of current social networking are not on target with the needs of patients and professionals in medicine and healthcare. While a user may seek out a community that has a targeted illness to connect personally, the community lacks an infrastructure to aid, assist and facilitate diagnoses, resolving symptoms, interconnecting communications as to treatments, medicines, access to resources, funding, or expertise in medicine. Further, while patients are not able to find resources via social networks, professionals in medicine, such as the medical provider, doctor, surgeon, nurse practitioner or other health professional is not able to interconnect with medical professionals globally, or in confidence, unless a prior connection is known from prior encounter or via word of mouth.

A need exists for an electronic system, a social network that can interconnect patients, families and friends of loved ones who desire information upon diagnosis to properly resource their needs for knowledge of not only the disease, but including personalized connections to others who suffer and heal similarly. The individuals of the social network of patients will beneficially be able to share their experiences publicly across the network to interconnect with others, interconnect with medical professionals globally, and/or obtain comparisons in medicine from other patients and/or medical professionals. As well, the medical professional network will allow a doctor, surgeon, nurse or otherwise to expand particular knowledge base(s) as to diagnosis and treatments across the world's medical communities. The following will beneficially detail the possibilities of solving such needs and implementing the technological measures to achieve the same.

SUMMARY OF THE INVENTION

High speed networks across the web and cloud computing have evolved into interconnections to facilitate networks around the globe. The health network system described herein resolves the issues described above by addressing the professional use of social networks and real-time access to patients and medical professionals around the world.

The network of healthcare resources (1) targets market needs (customers), (2) utilizes federal and state funding initiatives (economic growth), and (3) revolutionizes medicine through innovation, translational research (clinical focus), commercializing and updating data systems for predictive analytics and deep learning for easy access data in healthcare delivery.

The health networking system and methodology targets the personalized and global community needs in medicine and healthcare to interconnect information as to diagnosis, symptoms, treatments, side-effects, and chronic and acute conditions, among others, further addressing short-term and long-term effects and recurrences. The network seeks out individual users in a community or across the globe with similar ailments or medical conditions, and may include those users with professional expertise. While a user may seek out another individual or community that has a targeted illness to connect personally, the community is formed via a computer-based infrastructure that facilitates the network connections of users. The users can correspond as to diagnosis, diseases, symptoms, treatments, side-effects, use of particular medicines and/or natural supplements. The system provides access to resources, funding, and expertise in medicine as well.

The health network system allows patients to find resources via social networks, professionals in medicine, such as the medical provider, doctor, surgeon, nurse practitioner or other health professional, and suggests possible interconnects across the globe, either with other patients, family members, and/or medical professionals. The communications are private as selected via a user profile and shared with those who desire to interconnect. Any privacy information shared is therefore at the discretion of a user and not subject to regulatory laws where a patient provides details of his/her condition.

The electronic system is a health social network that can interconnect patients, families and friends of loved ones who desire information upon diagnosis to properly resource their needs for knowledge, specifically personalized knowledge from not only online resource dictionaries, but directly from patients or those being treated for similar conditions, from those who are also suffering from an ailment, or healing from disease. This emotional support network satisfies deficiencies in current social networks. In addition, social networks have failed to accommodate the mental health communities, such as those with post-traumatic stress syndrome (PTSD) and stages of depression; the current health social network provides for a network to confidentially communicate and manage emotional, psychological, and psychiatric needs to better mental health for patients and quality of life. Furthermore, users with mental health conditions can discover individuals with similar ailments, concerns, or even discover friendships to alleviate the unsatisfactory conditions that cause deficient or unhealthy mental states.

Further, the health network is a progressive online network to focus on individual and globalized health needs, studies in epidemiology, medical education, and professional development. Data collection and analytical systems will utilize the data to predict outcomes, treatments, disease, utilizing predictive analytics, machine learning, deep learning, and detailed to expansive artificial intelligence (AI) social networking health system.

The system utilizes the connection with medical professionals including doctors, surgeons, nurses, nurse practitioners, pharmacists, podiatrists, psychiatrists, among others to connect with his/her specific patient and interconnect on a backend of the network with the doctors or medical professionals interconnected with patients who have opted into the network. The health social network therefore allows medical professionals to post, message, or provide advice, if practicable, and to post, message and directly connect with another medical professional of the interconnected patients to build an expanding collegial network.

The individuals of the social network of patients will beneficially share their experiences publicly across the network to interconnect with others, allowing medical professionals to interconnect globally within ethical constraints. The system not only expands upon a network with personalized and comparison medicine; the system factors in attributes such as geography and environmental characteristics which could impact epidemiological studies and address global health conditions. Additionally, the remote and mobile access allows interconnection across the globe, within urban high tech settings to remote locations of the world with limited access to medical care and high end and/or affordable treatments. The health social network is a life line communication network to reach out to others with similar health conditions, from new moms to guardians caring for elderly parent, chronic conditions to acute disease, common illness to end-of-life care.

Operationally, the online health network can manage internal hospital social interactions among patients, physicians, hospital personnel, and further manage and review workflow. The data collected from the operational systems, including insurance management and payment systems, electronic medical records, and any of the above data entered by users to the system (i.e. patients, visitors, personnel, professionals, administrators, etc.) is then utilized in predictive analytics and AI to efficiently and effectively control costs in the delivery and management of healthcare, along with delivery of improved patient care through consistent decision-making and hospital authorizations.

Finally, the system shares and exchanges knowledge of Western and Eastern approaches of medicine, from the natural practices of the Amazon to the rainforests of Papua New Guinea, the reservations of Native Americans, North and South American medical practices, the practices of traditional chinese medicine (TCM), implementations of Ayurveda of India, and others known and unknown. From practices of medicine more than 3,000 years ago, utilizing concepts of health and disease that promote the use of herbal compounds, special diets, and other unique health practices, Eastern medicine can truly be implemented with Western practices.

By providing a connection across the hemispheres to remote and well-established regions of the world, patients and medical providers can now truly interconnect. Connections not known prior will be formed, allowing a revolutionized practice of medicine beyond the influence of politics and political regimes, beyond the influence of monetary wealth, and innovate all walks of life.

BRIEF DESCRIPTION OF THE DRAWINGS

The accompanying drawings, which are incorporated in and constitute a part of this specification, illustrate various embodiments of the present invention, and, together with the description, serve to explain the principles of the invention. The various features are not necessarily drawn to scale. In fact, the dimensions may be arbitrarily increased or decreased for clarity of discussion. In the drawings:

FIG. 2A is a schematic representing a patient interactive social network.

FIG. 2B is a depiction of an embodiment of a patient user interface.

FIG. 8 represents system development of databases, libraries of information, and creation of communities.

FIG. 9A corresponds to value add-ons in the system, such as recommendations, advertisements, availability of clinical trials, patients receiving particular pharmaceutical drugs, among others. FIG. 9B represents a patient user interface in one embodiment of the system.

DETAILED DESCRIPTION

Figure 1:
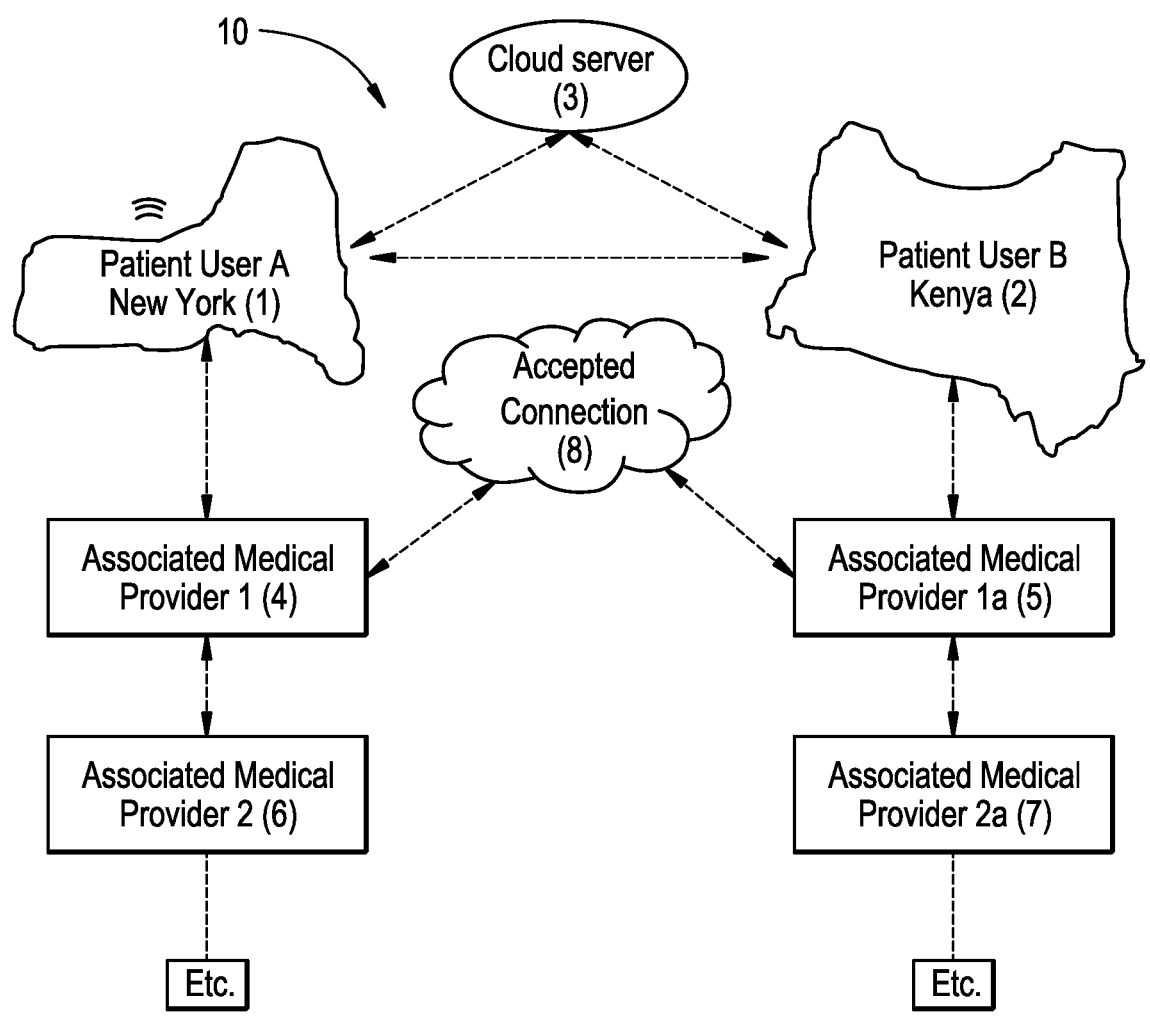
FIG. 1 is an exemplary schematic as to an overall health network.

Reference will now be made in detail to the present embodiments of the invention, examples of which are illustrated in the accompanying drawings. Wherever possible, the same reference numbers will be used throughout the drawings to refer to the same or like parts.

The health social network provided herein encompasses an individual patient, his/her family, friends, and/or associated medical professionals. While implemented regionally to obtain comparisons in medicine from other patients and/or medical professionals, the system is utilized globally to encompass and assimilate a volume of data not currently available in the health market without individual integration of medical systems. The data is patient managed and authorized for release to medical professionals (e.g. medical, dental, nursing, affiliated health professions in physical therapy, respiratory therapy, occupational therapy, or otherwise). As well, the medical professional network will allow a doctor, surgeon, nurse or otherwise to expand his/her individual knowledge base as to diagnosis and treatments across the world medical communities; and/or allow a health system to consistently manage symptoms as aligned with diagnoses, treatment options, alternative care and care plans. Algorithmic analyses integrates, collects, and analyzes the data based on the unique qualifiers, inquiries, and coding selected in the backend user and medical provider systems, both component parts integrated as one and accessible individually by cleared and qualified users. The following will beneficially detail the possibilities of solving such needs and implementing the technological measures to achieve the same.

A system disclosed herein is a health targeted social network that utilizes social interactions and connections of patient users to better understand disease, illness, symptoms, treatments, and side effects. The system pulls together a patient's associated medical providers, allowing providers to connect on a back end confidential portal, implement other resources such as clinical trial availability, global treatments and protocols, among others. Various interactions and connections are possible, the perspective view allowing patients and loved ones (i.e., friends and family) to seek out personal connections around the world with those having particular ailments, disease, or perhaps deciding on treatment options as based on another patient's particular reactions and experiences. The following is not limited to the described interactions and may be broadened to expand within privacy (HIPPA) approved domains, pulling in external databases, implementing user interfaces, changing the patient or client user to any friend, family member, researcher, clinician, medical provider, service or insurance provider, among others.

Of particular mention and novelty of the online health social network is the placement of healthcare in the patient's control; access to a patient's data is authorized by the patient or the family member or agent with authorization to release patient data. Such relationship that is frequented here is parent—child where the child illness would prescribe a parent login to the system to validate child medical data for medical provider access (at provider's option/participation) in a confidential portal for medical providers, and an emotional and social network for a parent to discuss symptoms, diagnosis, treatment plans, drugs prescribed, interactions with other drugs, behaviors, and other details related to a child's health. The parent's interaction with other parents globally, delivers a personalized educational background to personalize a patient's treatment plan, expand options, offer alternatives from one end of the globe to the other, from Western medicine to Eastern medicine illnesses to treatments and curative programming.

FIG. 1 illustrates an overview of an online social health network 10 facilitating network interaction between patients in different geographic locations. A Patient User A in New York State (1) creates a login and links to a Patient User B with similar medical condition (e.g. lung cancer) in Kenya (2). The cloud server 3 confidentially collects and stores the patient data. Patient User A provides information as to an associated Medical Provider 1 (4) while Patient User B provides his/her data to medical providers, here including an associated Medical Provider 1a (5). A number of medical providers can be associated including Medical Provider 2 (6), Medical Provider 2a (7), etc. The medical providers associated with each patient are then sent requests (as based on information provided by the associated patient and/or verified in a database that pools all databases of licensed medical providers including physicians, doctors, nurses, podiatrists, psychologists, clinicians, among others). A first licensed medical provider of a first associated patient will be authorized to connect with a second medical provider of a second associated patient, given the patient's authorization and consent via a disclosure process when setting up individual patient client-user profiles.

An online social health network system 20 is presented at FIG. 2A. Patient A enters data at data platform 11 to set up his/her patient profile 12 including name 13 and/or alias, background and/or medical history as voluntarily provided. Illness/disease 14, diagnosis 15, treatment and/or treatment options are also entered, and any data as so designated or requested in coding the platform for data entry. Patent B enters data at data platform 17 in a similar manner to establish a patient profile 18 as well, including name 19, alias, and detailed demographic information. In order for the health social network to operate, patients will voluntarily provide at least one or more symptoms, category of illness or disease 21, whether or not a diagnosed disease 22, treatment or medicine usage, among other data. This provides the interconnected tangible medical and health component to link client users and offer emotional support, educational knowledge from other patient's personal experiences, allow medical providers to discuss a patient's condition, behaviors, etc. The physician-to-physician contact or medical provider to medical provider communications occur on a shadow account ('Shadow Chart'), in other words, a backend user interface (UI/UIX) that reflects patient information, but limits view specifically to medical providers 24, 25. As such, associated medical teams 27 are formed, allowing a 'community' for medical providers to share patient data at data exchange 26 to include charts, histories (again, with privacy protections and full disclosure to advise patient user as to sharing of any information provided, included release of medical histories to medical providers in order to co-develop solutions globally). Without having a better understanding of patient epidemiology, particular circumstances and situations globally, in a more personalized and centralized universe of data, medical solutions will remain isolated by geographies and resolutions left undiscovered. The universal application of the social network here provides not only social interactions and support in illness and disease, but also medical expertise on a unified global network that protects patient's records while seeking alternative and various viable treatment options. The wealth of information shared and explored further allows a medical provider to assist in treatment of his/her patient while traveling or to assist with another provider's patient on the other side of the world (or even in a neighboring state or health system).

An associated network 28 is a medical network such as EPIC within one hospital system, indicating a geographic region 29. The medical provider networks (e.g. 24, 28, 31) interconnect via an access point 30 which may be stored on a server or cloud based, with confidential and secure cyber measures. Other medical provider networks 31 may also tie in as populated in a database and selected in drop-down menus (including geographic region, locality, etc.).

A patient user interface (UI) 31 is illustrated at FIG. 2B to include user profile information 32, illness/disease 33, name/alias/location 34, diagnosis 35, and course of treatment 36, treatment plan/alternatives 37, medical provider listing 38 or association network. The patient UI 32 also includes a messaging capability 39 in real-time as well as suggested connections, daily updates/postings 40, events, descriptions, details and suggestions as to recommended 'communities' within the network, ads seeking patients for clinical trials, medicines currently utilized in treatment, among others. A translation tab 41 also is available to ensure communication across global communities.

Figure 3:
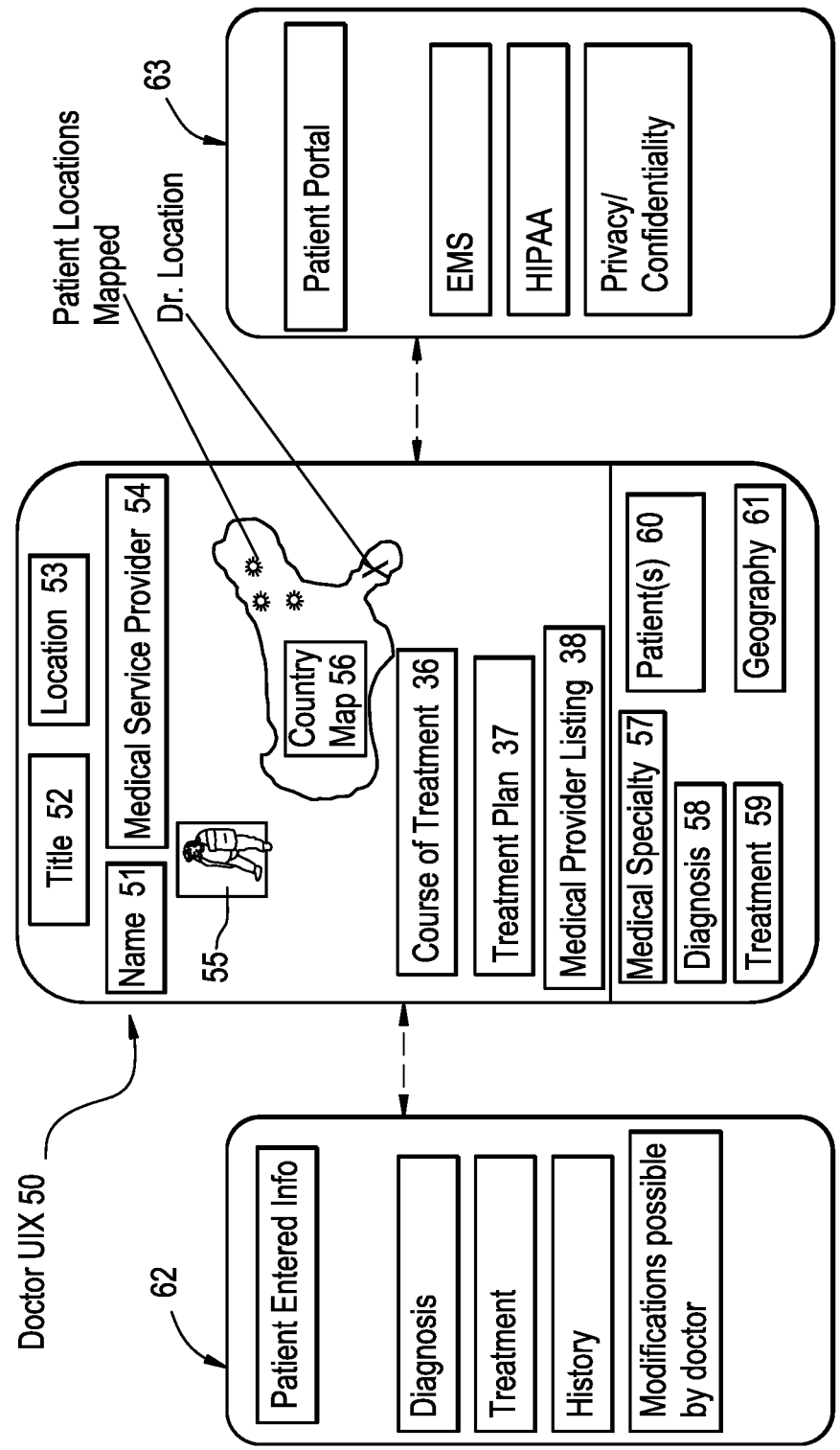
FIG. 3 is a schematic as to a backend interconnection of medical providers in a health network described herein.

FIG. 3 depicts a medical provider user interface (UI/UIX) 50, here, that of a physician based in the United States, and licensed in the U.S. The physician client-user UI 50 provides the name 51 and title 52 of the medical provider (e.g. General Surgeon, Oncologist, etc.), location 53, medical service/network 54 or health network he/she associates or is employed by, image/picture 55, geographic map 56 of locations served (i.e., patient locations mapped having similar illness/disease and doctor location), medical specialty information 57, diagnosis typical 58 (e.g. as designated by symptoms in database and generated by AI and data analytics), treatment options offered 59, and patients 60 associated therewith (e.g. names using aliases set-up and configured by the patient during patient's entering of information during initial configuration). Note that aliases, or de-identification numbers may be associated with a patient, as preferred and designated by the patient in initial profile set-up and disclaimer regarding data usage and analytics. The patient information 60 and geography 61 are selections for data analytics to pool and configure selections of data across the globe as to specified and personalized UI/UIX for physician guidance and consistency of care, as well as expanding knowledge base for diagnosis and broadening treatment options. Treatment options as associated with 'cure' rates and defining 'cure' may also be designated by physician and/or health system to determine personalized treatments and care for patients and goals for patient, provider, health system, insurance provider, operations, and government entities.

The doctor/physical UI 50 is similar to any of medical provider UIs that are viewable to the private physician client-users as access points to the network 10. The physician here can then associate, on a backend database, aliases with patient medical records, EMRs if authorized by a medical center having discretion in sharing HIPAA outside the medical division for medical provider use only. The physician can then confirm participation in the network to at least access patient profiles, see patient information pulled via patient portals and modify/comment as to any inaccuracies, or perhaps suggest/post as appropriate. Note that the allowance of medical provider access keeps medical providers in contact to share in patient information, data, and experiences with particular patients, etc.

While the social network operates to connect medical providers on a backend to share and grow knowledge of disease and treatment options, medical providers may also seek assistance from other medical providers as to diagnosis of a patient for any rare disorders (e.g., 'zebras'). The system may also gauge the involvement of a newly educated medical provider or physician who has limited clinical experience, and typically relies on book-based studies. The social health network system can personalize medicine and provide a larger scale community based medical program that takes into consideration vaccinations, epidemiology, environmental condition/circumstances, cultural practices, and details that may not be integrated with a patient's medical chart. Further, patient's are much more willing to share experiences with one another than with physicians and/or nurse practitioners who are strangers to their personal lives.

As shown in FIG. 3, patient entered data 62 appears on one screen. The patient portal 63 allows the patient to authorize release of medical and confidential health information, electronic medical/health records (EMRs/EHRs) and scanned written records, via privacy disclaimers and compliant with HIPAA and regulatory measures. The physician and/or medical provider may modify the data of the patient as entered or uploaded via the authorization by patient to ensure accuracy or validity, perhaps correction or clarification which can be conveyed to the patient as well. The medical provider may interact with the patient in private messaging portal as desired.

Figure 4:
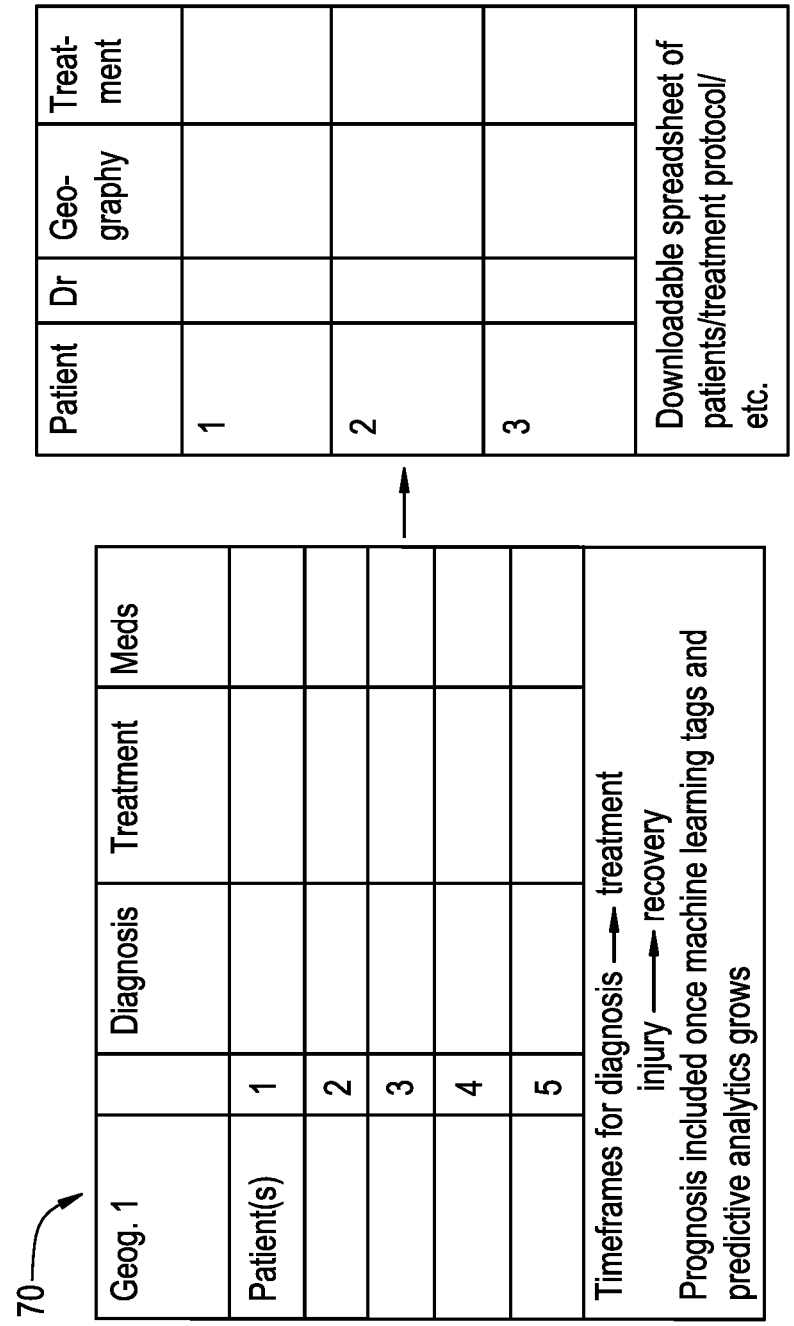
FIG. 4 is a graphical depiction of an embodiment that captures a presentation of selected data from the database and implements machine learning algorithms and predictive analytics.

In FIG. 4, a medical provider has access to one or more databases 70 that pools patients by alias created to look at data across time, geography, injury, recovery periods, treatments, symptoms, age, demographics, etc. Prognosis and diagnosis may also be integrated to include machine learning once data has accumulated, and predictive analytics capabilities develop to further grow the functionality and utility of the network to experienced medical providers, as well as to patients seeking social engagement and support networks in critical care decision-making.

Figure 5:
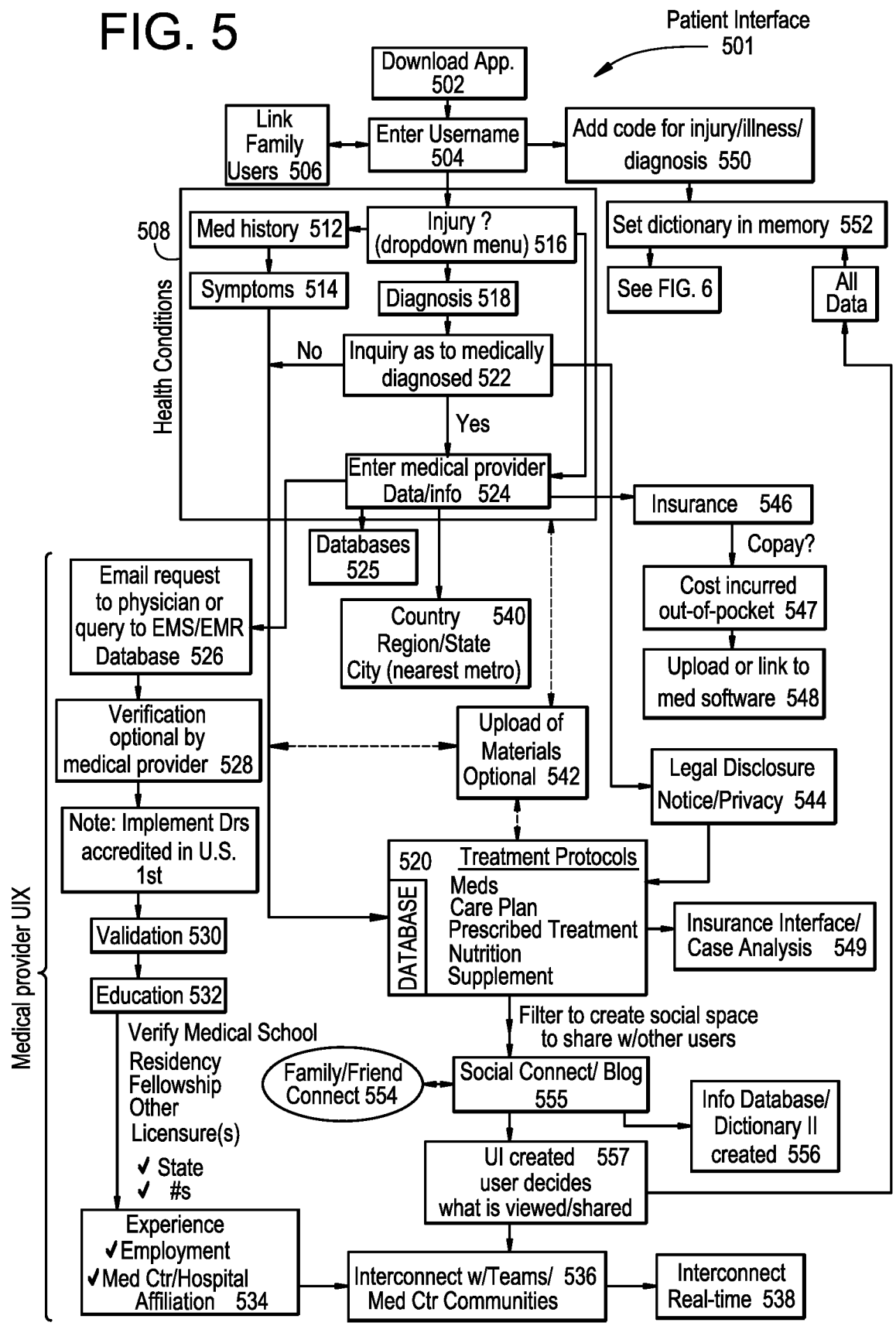
FIG. 5 illustrates an exemplary flowchart as to engaging interconnections within a health network.

FIG. 5 is an embodiment of the system disclosed herein describing set-up and usability of a patient interface 501 of a social health networking application 500. The website is available via mobile app or accessible remote from a desktop. The patient interface 501 includes an application (app) 502 that is downloaded to a remote device wherein a user profile 504 is created by entering a username, user information, creating an alias or nickname for back-accessed records by medical providers linked in the system. The patient user links friends and/or family members 506, colleagues, persons, and entities that he/she desires to share medical/health information, status, and updates with. The patient user then names health conditions 508, including medical history 510, ailments including, for example, symptoms 512, disease/injury 516, diagnosis 518, followed by in query to treatments and treatment protocols 520, among others. Drop down or menus provide options from a dictionary, the data entered creating, comparing, and selectively storing data in the dictionary as determined by algorithmic variations of terms, existing libraries of information, etc. If a disease or injury is selected, the flow chart proceeds to a next step of inquiring as to diagnosis, medical history, symptoms, and other variable informative details, inclusive of behaviors, activity levels, drug use, social interactions in society, among others. Medical materials and uploaded information 542 may be entered at the disease, illness, or treatment stage with warnings and pop-up disclosures/disclaimers 544 as to not releasing confidential or private information to the patient UIX. If not diagnosed by a physician, the database proceeds to an inquiry 522 as to suggesting medical providers, seeking care/treatment, alternative suggestions (not medical advice).

If diagnosed by a physician, the next query allows a medical provider name 524 to be entered. The system queries internal libraries and external databases 525 to select the appropriate providers, associated medical systems, accepted insurance providers, licensure information, educational background, prior treated patients, prior diagnosis-disease associated symptoms, treatments, clinical trials, etc. After pulling in as much data as available and extrapolated, the system sends an email or communication 526 to the medical provider. Here, the medical provider may be a primary provider, surgeon, specialist, or otherwise, such that the communication is by way of email, patient portal, health system query, or other electronic messaging so that the physician/surgeon can directly access 528 the medical client-user profile that has been set-up and confirm, verify, or modify his/her information. Where some information may be selected to be non-modifiable data, a help button or live chat will be available to provide and answer physician questions. This more appropriately addresses professional needs, concerns, desires, suggestions, and provides greater accuracy in populating expertise in the medical profession. As well, the medical provider enters demographics, geographical data 540 including country, region, state, city, nearest metropolitan area, or as specified by country designations. Furthermore, a licensure validation 530 and confirmation will be configured to verify identities of medical providers. As such, local, state, national and international licensure requirements may vary and be modified/implemented in different ways and methodologies.

At various steps along the methodology, the system has full disclosure, electronic signature acceptance of terms and conditions in utilizing the social health network. Terms and conditions may vary as based on patient client-user, physician client-user, and any person or entity/organization seeking a profile to establish or utilize the network communities. The educational background 532 of the physician/provider is queried manually to the user or to a database as to medical school attended/graduated, residency, fellowship, specialized education, licensure as to state, numbers, and as data is desired can be queried and coded, as appropriate. Experience data 534 is also included as to the physician/provider's employment status, medical or hospital affiliations, and any interconnected teams or centers 536 that are interconnected in real-time 538.

On a backend account, the physician client-user can verify an alias with an actual patient under his/her care and link to an electronic medical system/record (EMS/EMR). This disclosure is apparent to the client users even prior to setting up an account/profile. The medical provider/physician then can confidentially structure data in a database that will permit other medical providers access to information without complete identification of a patient. While this privacy/identification is often shared between different doctors and medical providers, this sharing of data and inadvertent use of such data by entities such as insurance companies, pharmaceuticals, and profit-bearing entities can be avoided by use of aliases in the system protected by the patient client-user. Therefore, physicians can interconnect with other physicians around the globe, access and track data of similar patients, or similar symptoms, behaviors, as selected and desired in a database. The interconnection of these physician based teams organizes 'medical communities' (similar communities of which are created on the patient accessible sites via the patient client-user accounts, as 'patient defined communities'). While medical communities are accessible by physicians and medical providers (via secure access and encryption), the patient defined communities are open to anyone in the social health network (patient client users, physician client users, etc).

By way of example, profit-based organizations and corporations may set up profiles to better understand cost, analytics of care, treatment options, procedures aligned with costs, align entities with particular procedures/costs. Such entities may include insurance based industry 546, Medicare/Medicaid based government programs, pharmaceutical companies, among others. Such data and access to cost based data is owned by the social health network and accessible by way of controlled data uploads per requested configurations. Cost incurred 547, including co-pays, out-of-pocket, premiums, and otherwise will be included as desired. An upload or link to medical software 548 external to the network may push/pull data through an accessible interface, or API that integrates the software without release private, confidential, or personalized data (i.e., data to be de-identified and confirmed as de-identified prior to any import or export). Any personalized data or patient data will be de-identified (by way of alias or otherwise) and by permissive use and contractual arrangements to better understand global needs, personalized and public health awareness. The system will address privacy and security measures, and make client users aware of public disclosure of health information attributable and responsible to the patient-user, and that any information not intended to become a part of public medical record should not be disclosed; and that any data entered will be stored in databases, de-identified, and may be sold for use in public health diagnosis, treatment, studies, research, and across the medical and health care fields of use.

Any insurance-based use of data 549 is utilized internal to the system for cost analysis and AI to better serve healthcare operations, administration, costs, pharmaceutical purchases, biomedical device purchases, and any incentivized payment structures or commissions as to payouts to hospitals, providers, representatives, among others.

Communities are established within the social health network are algorithmically determined and/or suggested by the system, or selectively personalized by a client-user, patient or medical provider. The client-user determines what his/her UI will share, or what is made viewable by other users. If a client-user wants to be included in future communities, have suggestions for such or otherwise, he/she can opt in or out. If client-user is a patient who simply desires to connect among family/friends, and create a health or support site, he/she may do that as well with minimal requirements to be entered into a shared database (e.g. disease/illness, symptoms, behaviors, activities, some basic medical info, and treatments, how long treated, planning, etc). This information has the benefit of epidemiological studies to allow trending data to be populated.

Continuing with the flow-chart of FIG. 5, a code 550 may be entered for an injury, illness, and/or disease to assist with algorithmic AI and deep learning for predictive analytics. Memory will assist in storing a set dictionary I (552) of data from external sources as to delegated and common names for disease, illness, treatment, medicines, and other material information.

Furthermore, FIG. 5 depicts a family-friend connection platform 554 that creates a social space to share with other users, patients or otherwise. The social connection or blog 555 will be tagged for use as metadata or searchable for key terms to create an information database, here dictionary II (556) for later analytics. The UI/UIX 557 created is what the user decides is viewed or shared, and by whom; the user decides what fields of data may be viewed publicly, privately, or via a select user community.

Figure 6:
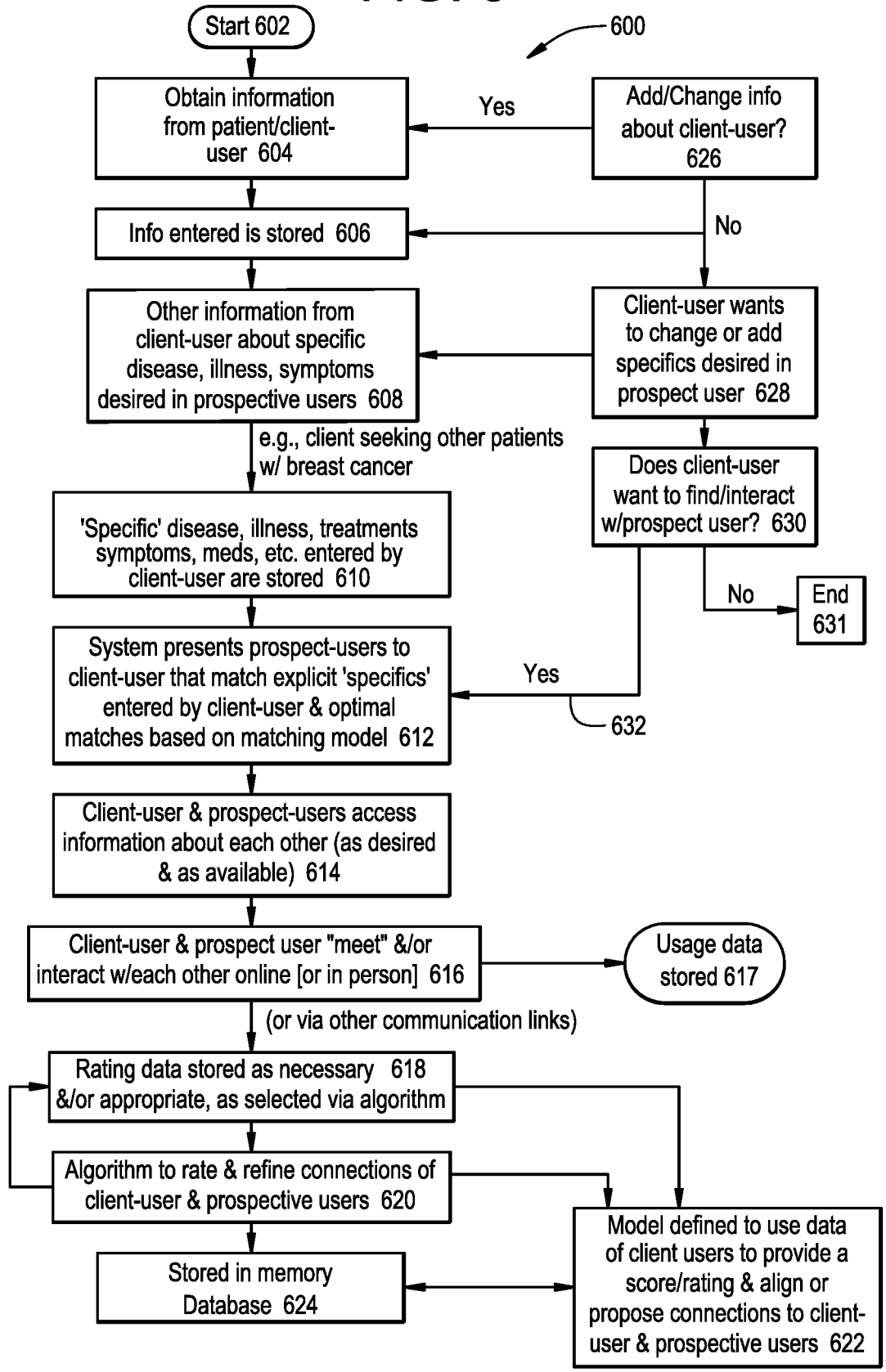
FIG. 6 methodology depicts operations of the network to include collection and integration of client [patient] user.

FIG. 6 implements a methodology as to entry and storage of patient data in the system 600. At the start 602 of the program, data/information from a patient client-user 604 (or client user who establishes a shadow patient user until the patient user verifies his/her account) is entered into the system and stored in memory 606. Other information from client-users specific to illness, disease, symptoms, etc, 608 as desired by prospective users may be entered. For exemplary purposes, and not limitation, a patient client-user with breast cancer seeking social interaction with other patients with breast cancer can select such affiliation. Specific disease, illness, treatments, etc thus are disclosed and stored 610 in order for the system processor to optimize profile alignments, as based on a matching mathematical model that suggests profile connections to a user 612. The client-user and prospect user access information about each other 614 (as desired and as available) to make a selection or de-select an online profile connection 616. Usage data 617 is stored as to social support network(s) established per disease, etc. Rating data is stored 618 as programmed and selected via algorithm refined 620 to rate and refine connections of client users and prospective users. Machine learning algorithms are utilized and models defined to use data of client users to provide a score and rating 622, and align or proposes connection to client users and prospective users. This information accumulates in the database 624. Predictive analytics of such data can be implemented to track patient information, data, and records around the globe, to assimilate Eastern and Western models of medicine for best treatment procedures and processes in personalized medicine (while protecting patient privacy and confidentiality, at the least, putting patients in control of their use of data, allowing an individual patient to determine what is and is not shared in the system in and shared networks). To the patient client-user, the benefit of socially interacting with others with similar disease and health conditions can be weighed against privacy and concerns for data.

Modifications in the data entry of FIG. 6 methodology allows the model defined 622 algorithmically to add or change information 626 about the client user, patient or doctor. This data may also be modified manually. Data as to the client user may be modified 628 as to additional diseases, ailments, illnesses, or changes status of disease, cure, or otherwise via the patient UIX, physician UIX, or algorithmically via data entries and patient portals of health systems such as EPIC or otherwise. An inquiry 630 asks a client-user, patient or physician whether that want to interact with prospective users 632. If no, the protocol ends 631. If the response is yes 632, the processing proceeds to matching mathematical model that suggests profile connections to a user 612. Modifications of the above may be customized and data entered, queries populated, as desired to conform to best practices in medicine and healthcare, and/or better treat and care for patients.

Figure 7:
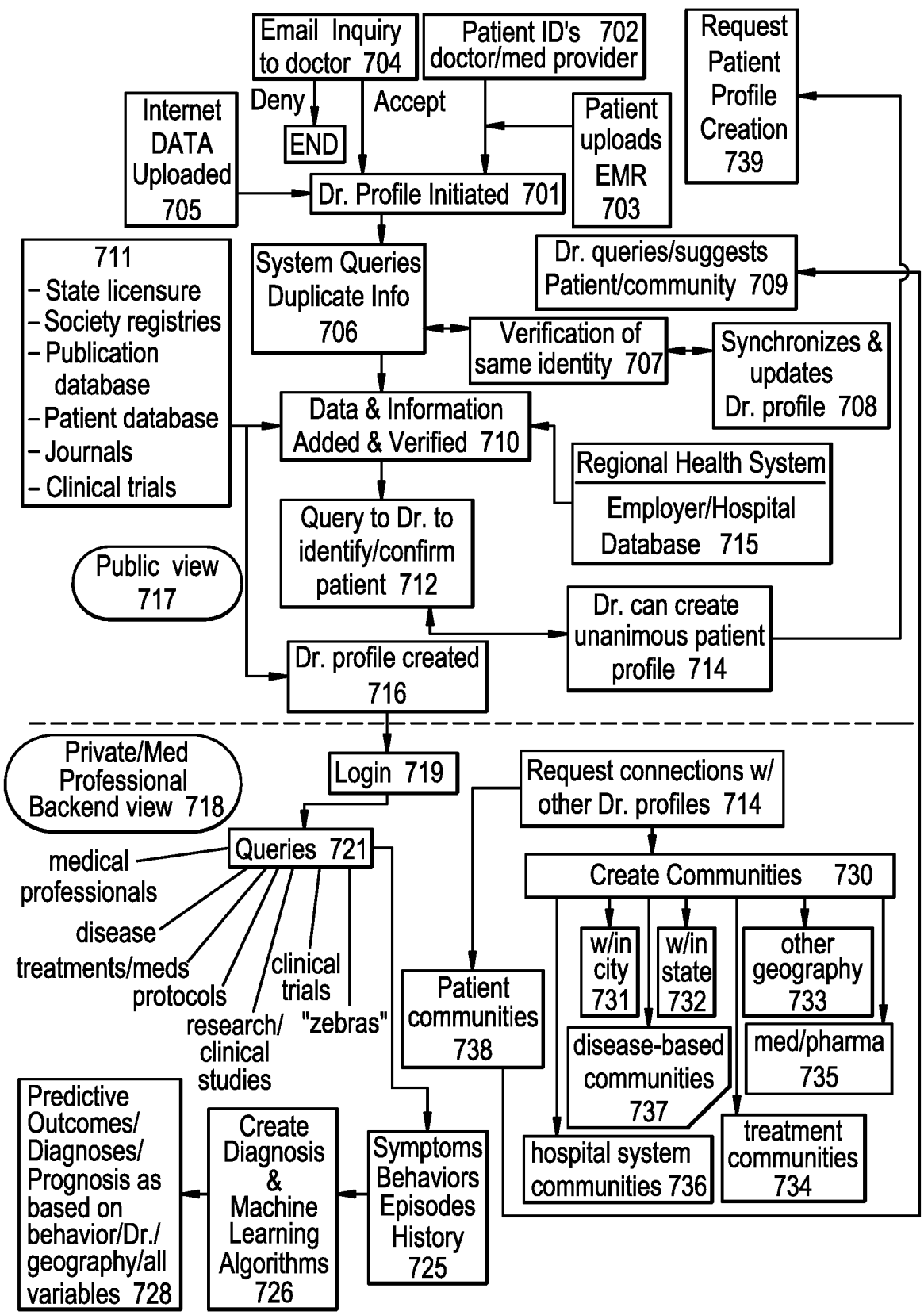
FIG. 7 assimilates information from a medical query to further engage a medical provider as a client user.

In FIG. 7, the flow chart demonstrates a medical doctor profile initiated 701. The social health networking application 700 includes a medical provider interface (UIX) 701. The medical provider may be implemented as any licensed medical professional, profiles established and associated with patients as patients designate 702 or as patients upload EMRs 703. The doctor may also refer or suggest 709*a* patient joining a medical community in the social network 700 via a patient UIX described prior. The medical doctor may establish a profile or be tagged/associated by the patient client-user in the system who answers the inquiry as to medical providers providing care. Here, an email 704 is sent to the doctor. If doctor declines, the system will continue to use the standardized information pooled from public databases 705 to populate the medical doctor profile account. As demonstrated here, if the doctor accepts the request, he/she will be directed to verify information 706, modify and confirm data 707 as to profile data 711, including, among others, licensure, society registries, publications, patents, journals, clinical trials associated with. The data is then synchronized 708 and updated in the physician UIX profile; and implemented at step 710 in the process. The doctor will further identify and confirm the patient 712 of the patient client-user with whom the email had been directed from. Where a patient does not opt into the system, a doctor may create a unanimous [coded/de-identified] patient profile 714 such that the later participating patient user would validate information in order to login and avoid duplication of an account or falsely create data. Information from the doctor verifies regional health systems and employers/hospitals that the doctor affiliates with. The medical doctor profile is created 716 is a medical provider licensed with the state or nationally/internationally. The doctor can access a public view 717 without patient EMR data and strictly what patient users have authorized. Otherwise, the doctor can access the professional portal 718 via the backend secure view where the doctor can login 719 and request connection 720 with other physicians in the global health social network 700.

Public view 717 of the physician profile may be similar to private, such as doctor background, licensure, etc. Patient data, if visible, from a physician or medical provider profile is de-identified by way of alias or otherwise. Physicians cannot pull direct patient identity from an EMR into the system, and if so, it is only viewable by other physicians. An encrypted login, possibly by way of digital certificate, allows a doctor to relate a specific EMR, or group of EMRs, to a customer number (e.g. number associated with a patient, or perhaps associated with a health system such as Lehigh Valley Medical System, or Oschner Medical System, or Willis Knighton Hospitals), and securely login to access identified patient data from the backend shadow patient profiles. The backend 718 shadow patient profiles are created by physicians who redirect EMR data and privacy information into a secure database 715 accessible only by licensed physicians, licensure as consented to by patients and providers of health systems to share in medical privacy information of patient in overall care and delivery of healthcare/medical services. As depicted, the secure database is a regional health system portal and/or employer/hospital database 715.

The queries 721 of the physician are directed to medical professionals secured in the network 700, diseases existing or unknown (and categorized symptomatically), treatments, medications, protocols, clinical trials, research and clinical studies, funded studies via government and industry, "zebras" (e.g. unknowns and rarities); symptoms 725, behaviors, episodes, history, among others are included variables and sources of data collection, without limitation. The diagnosis created may be generated via existing databases, and further queried and populated into databases via algorithmic data collection and analyses, machine learning and AI 726. Predictive outcomes 728, diagnoses, prognoses, as based on behaviors, doctor's profile in treatment, education, training, and geographical variables will be capable of being implemented in decision-making trees for improved patient care, outcomes, operational efficiencies and cost-effective measures.

As depicted in FIG. 7, communities 730 are created to align patients within a particular geography (i.e., city 731, state 732, country, continent, or other geography 733; or perhaps within a particular typical biome (e.g., rainforest, grassland, desert); or at particular global latitudes (e.g., equator-based diseases, death rates, depression; sub-tropical medical conditions; seasonal behaviors). Communities within the social health network may be patient designated communities, doctor or medical provider characterized communities, defined by med/pharmaceutical entity client-users, insurance client-users, government-based access, and any number of one or more of the listed, individually or in combination, varied and diversified. The communities may be suggested by learned algorithms of the system and recommendations for communities, or recognized trends communicated to client-users who would benefit from the community information or pooling of particularized data (data learned and client-users learned from deep learning based algorithms). Predictive analytics can help forecast future needs, anticipated openings in clinical trials, combinative treatment options, variations in acute and chronic treatment options, etc. Diagnoses may be addressed or even achieved where symptoms can be input and data sourcing optimized to relay prior treatments and success and/of failure rates. Episodic treatments and the movement of patients from one provider to another can also be tracked and care continuously provided for any illness and/or injury. Treatment communities 734 may be established manually or algorithmically through AI and deep learning to better understand treatment plans, personalized medicine, and alternative treatment options globally. In addition, medical device and pharmaceutical drug use 735 may populate communities for sharing parts and performance information (e.g. spinal implant groups, among others). Hospital system communities 736, disease-based communities 737, and patient-created emotional support communities 738, or otherwise may be created and established as determined by a user and led by patient or physician.

A community may request a patient user create a profile 739, request participation of a patient, or perhaps participation of another provider, physician or specialist.

In addition, surgical teams may find benefit here where teams operate on efficiencies in hospital operations and pay-for-service, e.g. anesthesia teams and anesthesiologists having access to patient care records, prior surgical records of a patient, prior operations, use of cannulas, medications, etc. Real-time video conferencing through the UIX with cybersecurity measures further allows a direct access to support networks, group chats, and face-to-face virtual meet-ups where immune systems are compromised and/or mobility limited to participate otherwise. As such, the medical provider profiles created would pull in patient data from patients of the surgeons, and invite/assemble medical teams, representatives of medical device and pharmaceutical companies, and operating room (OR) teams to better manage a patient and procedure effectively and efficiently under cost efficient and safety measures or concerns.

FIG. 8 demonstrates an embodiment of a system 800 that pools data from a physician and/or surgeon profile 801 including background education, medical schooling, residency, fellowship information, medical patients, outcomes, etc and streams that data into a shared database 805. Patient client-users 802 enter a profile with individual patient history, behaviors, etc. and view a disclosure authenticating use and permission to extract EMR 803 from patient record to the physician account/profile (identified/de-identified for sharing with other medical professionals and de-identified for profit-based healthcare or pharma/biomedical industry for purposes of enhancing healthcare delivery globally and providing of health services.

If permission is not granted by patient to extract EMR from hospital/provider network, the patient uploads or enters data and limited data is provided to verified medical provider confirmed databases and servers. A first database stores 807 this entry and use of data by a processor 811 to recommend connections. Data, images, medical info from the patient can still be uploaded 806 and provided for profile extrapolation.

Where patient client-user authorizes access of the system to his/her EMR for use in the health social system, the system provides notices 804, including a liability waiver, legal notices, privacy and compliance disclosures to be acknowledged 809 by patient client-user. Any data not entered via EMR may be entered 806 from patient uploads, and read via bots or algorithmic identifiers created to read EMRs. The patient client-users (whether including EMR or not) identify suggested and prospective users 810 by searching medical condition or disease or diagnosis (or any search request based on health care or condition). A processor recommends corrections and/or connection 811, communities 812, as based on data entries. Updates and verifications are affirmed 813. If at least one patient client-user or 'shadow' patient client-user account/profile, data is stored 815. Doctors and medical providers can recommend 816, refer, or create communications between patients 817, share postings or profiles, communities, etc. A separate professional/medical oriented database of medically licensed can establish backend secure communities 818 as well, and/or create personalized patient networks.

FIG. 9A is a value ad-on to the system that allows communication to client-user profiles, here a doctor client-user 902, as to learned patterns and data structures how a client is using the system. Ads 903, 904, 905 and/or pop-up may present on the UI of the profile, changing as based on client-user use. For exemplary purposes, and not limitation, the system may populate suggested medical facility data 906 related to one or more patient client-users. A notice may stream across the bottom of a screen as to clinical trial availability. Another ad may be suggested as to medical basis, disease, or learned processes and treatments; otherwise a pop-up may provide outcomes globally suggesting particular treatment options or medicines. Pharmaceutical or medical device companies may advertise here, insurance display as to cost-basis and baseline medical treatment costs for procedures or particular medicines utilized by doctors.

FIG. 9B is particular to an embodiment of advertisements (ads) utilized at a patient client-user UI 910, including availability of facilities/hospitals offering active treatment programs 911, clinical trials 912, and/or pharmaceutical drug or device ads 913. Social events 914, 'community' fundraising opportunities within the network, on other online programs, or society based fundraising live events. Other ads and possibilities exist as to potential opportunities for value add, cost savings and efficiency in medical care services. Further, enforcement of regulations, e.g. Stark, Anti-kickback, FCPA, and preventions of fraud or misuse of data can be implemented and disclosed here and in profile based set-ups.

Figure 10:
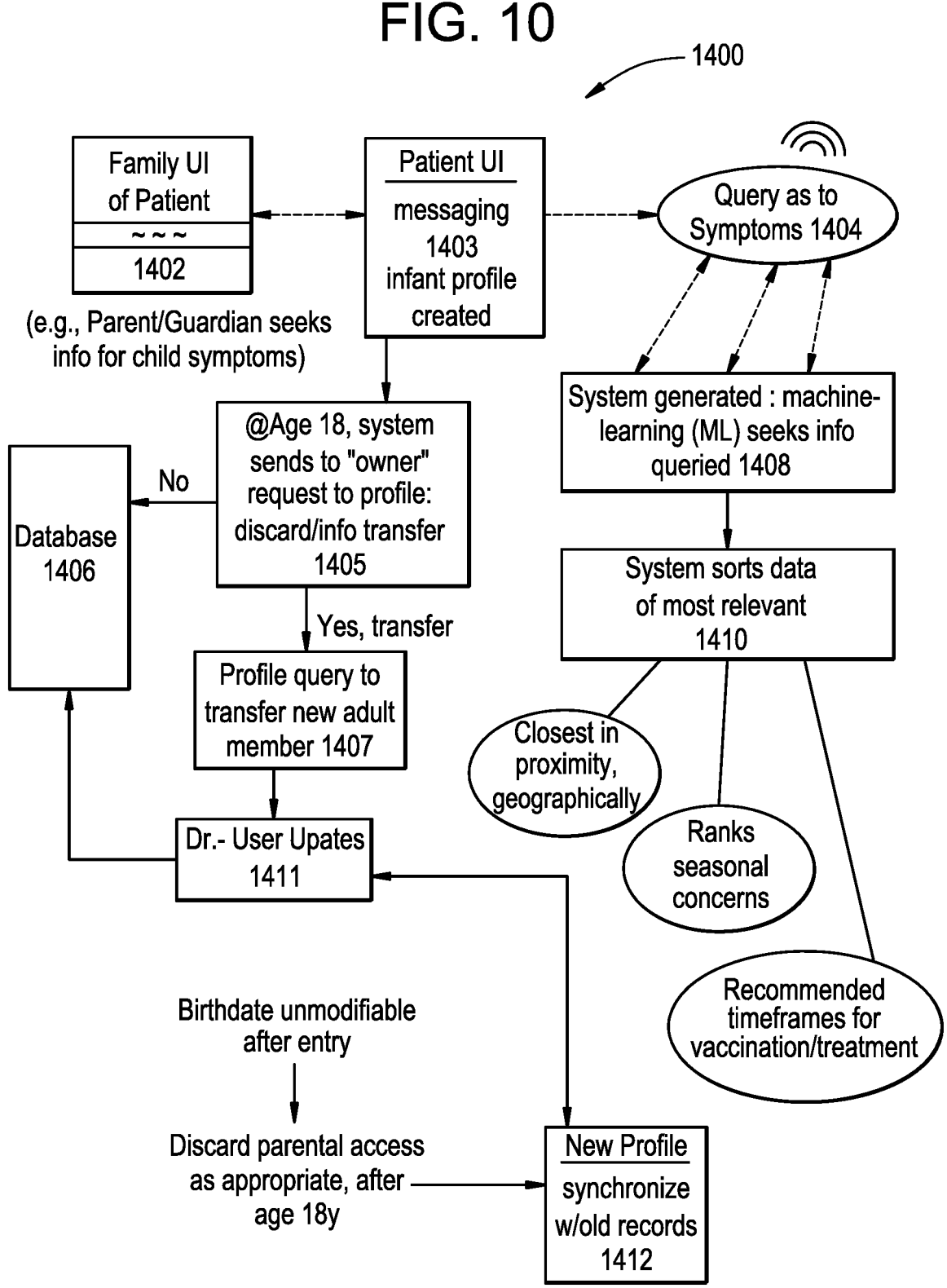
FIG. 10 illustrates an embodiment of the social health network whereby a family member and/or friend interconnects with the patient client-user, or can set up an 'echo' or shadow profile for a known patient that can request patient join.

A family member client-user profile can associate and attach a patient profile as shown in FIG. 10. The family member may also be a friend, colleague, or otherwise. If the patient has not authorized or setup a patient client-user profile, then the family member client-user (or guardian type client-user) can establish a shadow patient profile to gather social and emotional support across a network, connecting with other family members who are in similar situations with children, aging parents, etc. The emotional support offered within the network among the caregivers of loved ones is also a substantive network of connections to bond, understand and better deal with watching a loved one/patient suffer, deal with pain, etc. Caregivers also seek emotional and support that medical and healthcare systems cannot adequately provide for unless displaying symptomatic and medically treatable conditions. The health social network here allows those caregivers to better connect and understand treatments, options, care, etc, emotional support and resources that often get overlooked in the primary care of the injured/diseased patient.

Note that FIG. 10 also allows the system 1400 to query and to sort most relevant data as to trends, reoccurrences, increasing geographies or spatial relations globally, recommending vaccinations, treatments, etc. Perhaps the family client-user 1402, here, is a parent of a child who has now reached his/her 18$^{th}$ birthday 1405 in the United States (other considerations of 'adult' provided for as based on country of other users). The owner of the shadow patient account 1402 receives a notice and request to transfer or discard patient related information. If discarded, the data remains de-identified in a database 1406. If transferred, the system generates communication or recognizes a profile entry of a new adult patient client-user 1403 as synchronized with prior account set-up 1407. Note that birthdate would need be a confirmed entry by a medical provider at time of profile set-up by patient client-user who pulls in EMR data, the birthdate later being unmodifiable. After a notification period, e.g. 90 days prior to shadow patient user account aging 18 years, the account would invalidate parental or family member access to that account. Otherwise, a shadow account would become inactive unless reconfigured via a link in the system and verified identities. Again, separate databases would ensure verification and validation of various forms of data.

In system 800 of FIG. 10, a query 1404 into symptoms of the patient generates a machine-learned algorithmic result or solution 1408 to sort relevant data 1410 as to closest proximity of ailments geographically, ranking seasonal concerns, recommending timeframes for vaccinations/treatments, and uploading physician UIX 1411 info into the updated database. In combination with converting an adult profile 807, the new profile is capable of synchronizing old records 1412.

Figure 11:
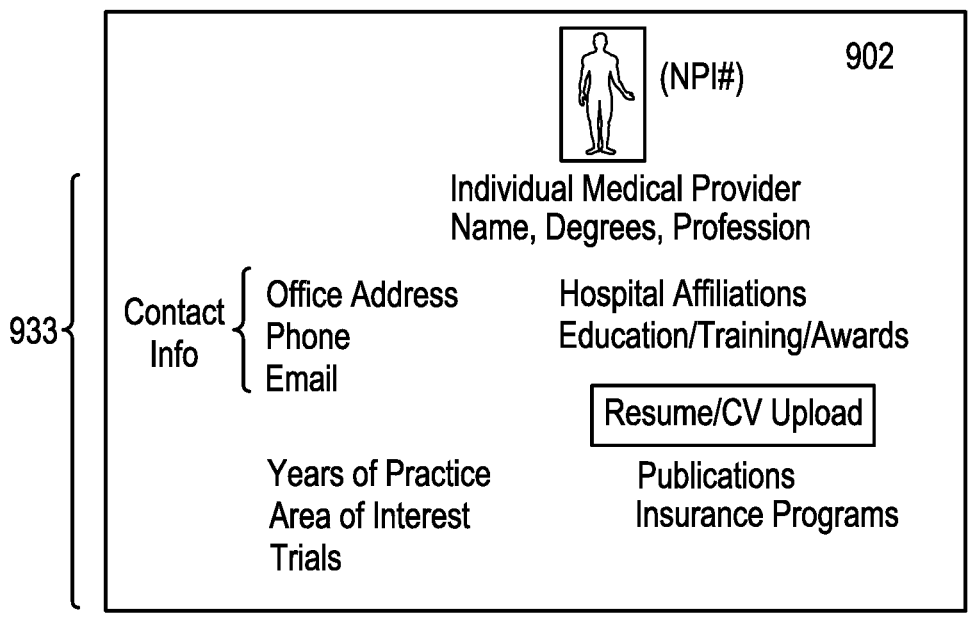
FIG. 11 illustrates an embodiment of a doctor profile.

FIG. 11 depicts an embodiment of a doctor profile 902 with image, provider demographics 933, including name, degree, profession, address and other contact information as appropriate. Hospital affiliations, education, training, awards, and resume/CV (curriculum vitae) upload are apparent. Years in practice, areas of interest, trials, publications, insurance programs also are listed. Resume upload is sortable, compliable and capable of being scanned for data.

Figure 12:
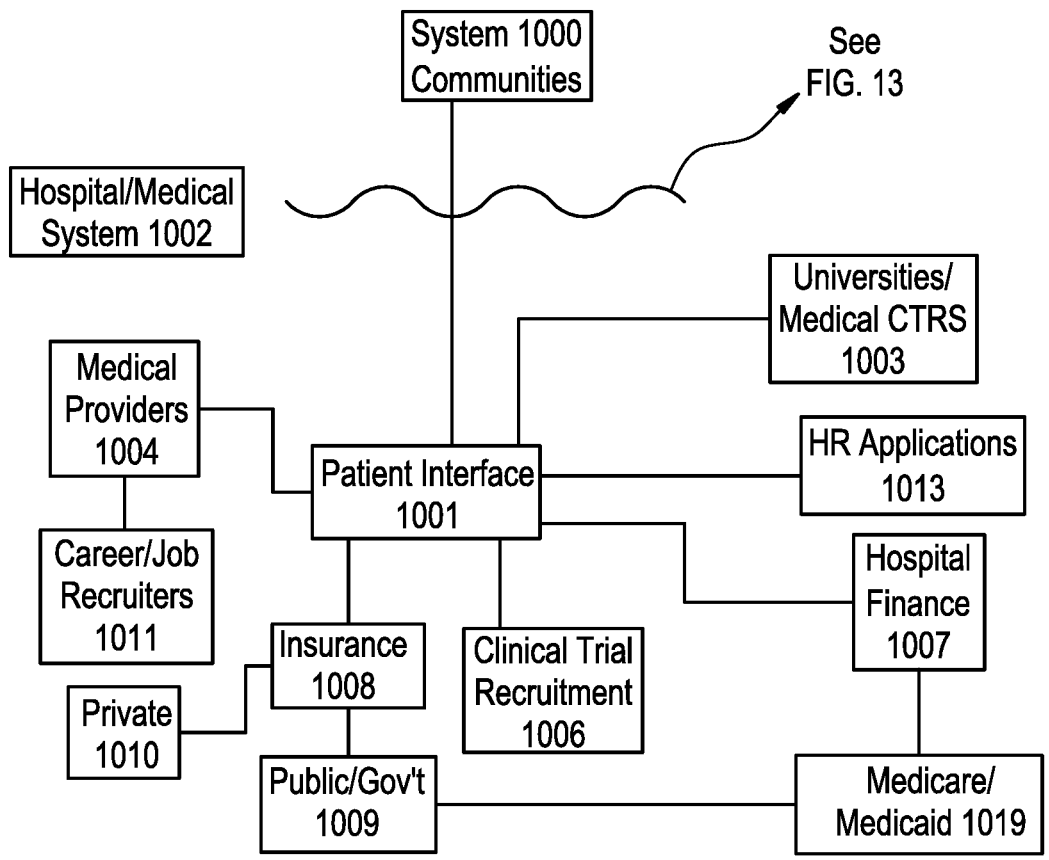
FIG. 12 depicts an embodiment of various users in a defined community within the social health network.

FIG. 12 demonstrates various examples of system communities 1000 without limitation. Such communities are built around a patient client-user interface 1001 to include hospital/medical system communities 1002, university medical centers 1003, medical provider communities 1004 (linking to career/job recruitment), insurance communities 1005, (private and public), clinical trial recruitment 1006, hospital finance 1007, insurance communities 1008 including Medicare/Medicaid (government) access communities 1009, and private insurance 1010, human resource communities 1011 for much needed clinicians, doctors, nurses, among others.

Figure 13:
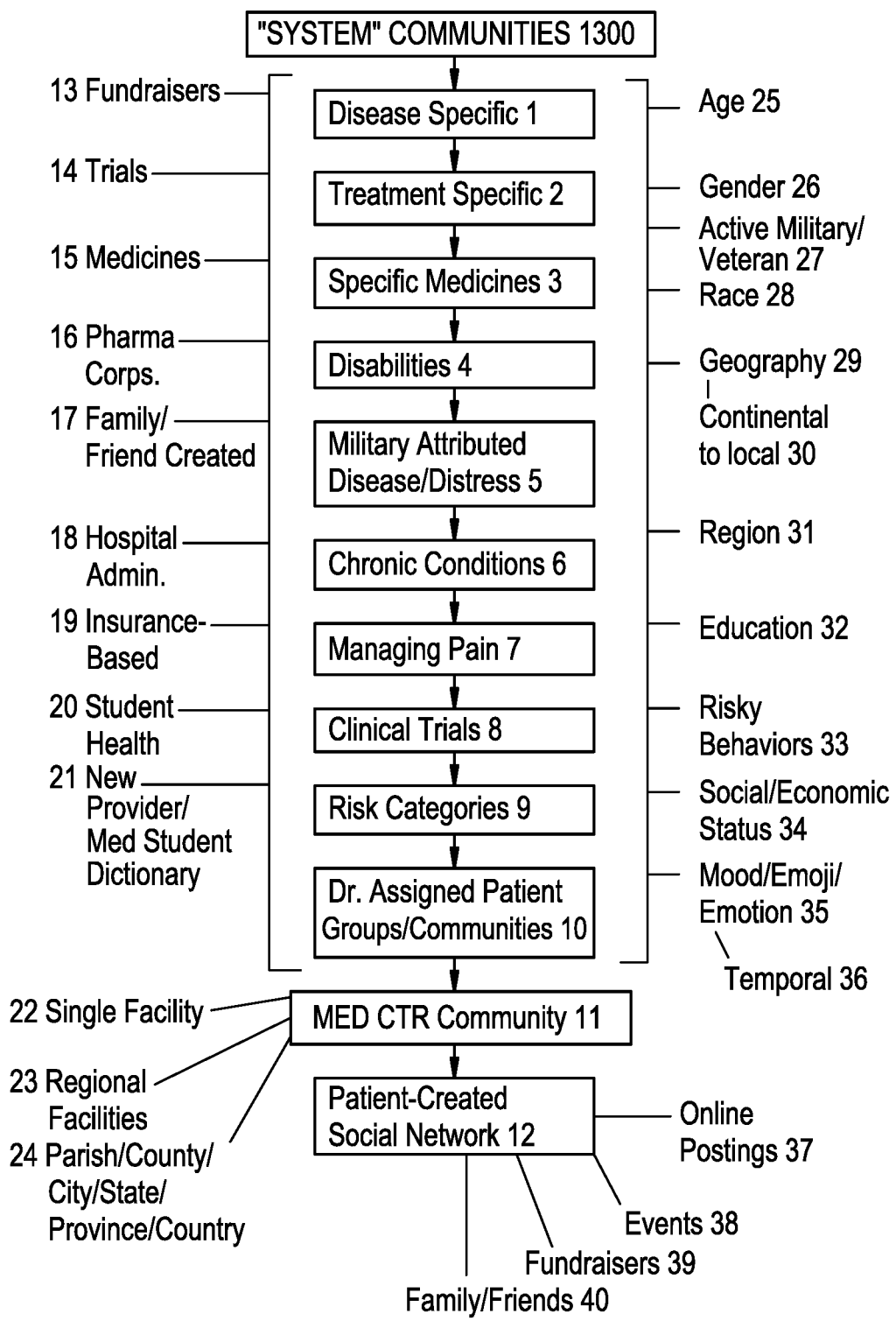
FIG. 13 illustrates a representative social health system of communities, possible to be configured selectively and/or automatically.

FIG. 13 further sets out the system communities 1300 as defined in the online and cloud-based social health network. The communities may be specific to disease 1, treatments 2, medicines 3, disabilities 4, military/war activities 5, travel, chronic conditions 6, management of pain 7, clinical trials 8, risk categories 9, behavioral risks, doctor-assigned patient groups 10, patient created social networks 12, caregiver support groups. The provider based system demographics range from medical schooling, prior treatments/care provided, facilities, geographic location, seasonal demographic, biome, pharma, trials, fundraisers 13, new treatment options, Eastern and Western medical practices. The patient demographics also looking at age 25, gender 26, military/veteran service 27, race 28, geography 29, continental/local 30, region 31, education 32, risk/behaviors 33, activities, socioeconomic status, mood 35, emoji/emoticons included with emotions (i.e. temporal and trending via treatment course 36). The UIs of medical provider and/or patient client-users will be similar to functionality of commonly used social networks today, including and not limited to, image uploads, status changes, events, activities, relationship associations (here linked not only by family or personal relationship status, but also linked to patient relationship, possibly 'caregiver' status). In addition, the system may include Xray or MRI uploaded information or slices of CT imaging, blood sample results, testing, etc. A patient may upload to his/her preferences. The EMR portion, however, restricted to medical provider access. Any restrictions and/or limitations may be modified in context of regulatory measures and laws across the globe.

Furthermore, federal and international databases can be integrated as resources and tools in the network for the social network user. Such databases may include for example and not limitation, the NCCIH Clearinghouse (providing information on NCCIH and complementary and integrative health approaches; www.nccih.bih.gov), PubMed® (a service of the National Library of Medicine comprising publication information from scientific and medical journals; www.ncbi.nlm.nih.gov/pubmed/.node), the Cochrane Database of Systematic Reviews (evidence-based reviews produced by the Cochrane Library, an international nonprofit organization summarizing results of clinical trials on health care interventions; www.cochranelibrary.com), NIH Clinical Research Trials and You (website created by NIH to help people learn about clinical trials, why they matter, and how to participate; www.nih.gov/health/clinicaltrials/.node), Research Portfolio Online Reporting Tools Expenditures & Results (RePORTER) (a database of information on federally funded scientific and medical research projects being conducted at research institutions; www.projectreporter.nih.gov/reporter.cfm).

The electronic system, a social health network disclosed herein, interconnects patients, families and friends of loved ones, who desire information upon diagnosis to properly resource their needs for knowledge of not only the disease, but including personalized connections to others who suffer and heal similarly, to caregivers who also demand emotional support. The individuals of the social network of patients will beneficially be able to share their experiences publicly across the network to interconnect with others, interconnect with medical professionals globally, and/or obtain comparisons in medicine from other patients and/or medical professionals. As well, the medical professional network allow a doctor, surgeon, nurse or licensed medical provider to expand their knowledge base as to diagnosis and treatments across global medical communities. The social health network beneficially details the possibilities of solving the needs for social support networks in medicine, the interaction of medical professionals and access to global patient data, while implementing the technological measures to achieve the same. The system goes beyond expectations for care and treatment of patients, providing a support network for caregivers, and also revolutionizing the training and expertise of medical professionals. As well, escalating costs for healthcare services can be addressed in a more analytically driven methodology, providing consistency and efficiency in medicine. With a roaming population of individuals, patients, caregivers, and medical providers, travel has demanded access to patient care that is not currently provided; the social health network described here provides that capability. Medical providers and patients can similarly access and seek medical treatment and care globally, including support networks and emotional ties and connections that no other system has readily made available in healthcare.

In addition, methods disclosed herein analyze social method of analyzing social interactions to present content of interest to a user as selected by a recommendation unit. Much like the various social apps, this program is designed to encourage social interactions among users with similar interests and health conditions. When using a social networking system and viewing a webpage that includes information provided by the system, social interactions are allowed and recommend interconnecting. Certain types of social interactions are monitored and detected, recommending particular connections and identifying users based on a description of the interaction desired. The recommendation suggests the user engage another user in the social health networking system per health-based classifications. Any modification of information or use of the above may include any number of variables be implemented and modified to achieve the same and does not depart from the spirit and scope of the disclosed invention.

What is claimed is:

1. A system for management of healthcare to support a social health network comprising:
   a patient user interface customized by a patient user of the social health network and accessible from a first device;
   a plurality of patient controlled electronic health records (EHRs), each EHR having a patient record associated with a patient, the EHRs shared with a plurality of health provider systems and external databases;
   a data analytics platform comprising: one or more processors and at least one memory programmed to implement a network learning model, the network learning model generated from a training network to update one or more data sets comprising patient inputs, patient data from the patient record, and health provider data, individually or in combination, wherein the patient user interface provides an artificial intelligence (AI) generated depiction of data extracted from the one or more data sets or the network learning model, and customized from data of the patient user and the health provider user to create knowledge graphs personalized to the user and trending data characterized by data selections specific to the patient inputs, a diagnosis or treatment specific to a patient, and selections of health provider data;
   one or more servers to store the updated data sets in at least one database, and programmed to create at least one patient profile through the patient user interface and at least one health provider profile associated with the at least one patient profile and accessible via a second user interface, the one or more servers further programmed to:
      receive a request from the patient user of the social health network at the patient user interface to authorize release of the information associated with the patient user at an external system where the patient record of the patient user is stored, wherein the information requested comprises information identifying the patient user and a health provider user associated with the patient user in the social health network;
      access the database by way of the processor, wherein the processor predicts data models in personalized health diagnosis, outcomes, treatments, disease, healthcare operations, administration and cost, and alternative suggestions using deep learning algorithms that analyze the data sets;
      determine if the external system is authorized to transmit the information requested;
      in response to a determination that the external system is authorized to transmit the information requested, process the request and extract the patient record of the patient user from the external system to provide extracted data of the patient user;
      transmit the extracted data directly to the social health network;
      separate the extracted data into subsets, wherein a first subset comprises health information with the patient user identified and available to be shared with the social health network, and a second subset comprises health information of the patient user available to be shared with the social health network when the patient user is de-identified;

de-identify a portion of the second subset of the extracted data to provide de-identified data of the patient user;

in response to a query or selection by the patient or the health provider user, the processor is directed to extract, sort, and trend data, the de-identified data, or any subset thereof;

wherein the step to de-identify occurs prior to the step to perform data analytics, thereby protecting privacy of the patient user; and transmit one or more predictive suggestions or outcomes to at least one of the patient user interface or the second user interface as a personalized depiction of data generated by the patient inputs or health provider inputs in combination with the generated AI.

2. The system of claim 1, wherein the patient user authorizes the health provider user access to the subsets of the extracted data at the second user interface.

3. The system of claim 2, wherein the second user interface is customized by a health provider to present real-time data analytics in a graphical depiction using the de-identified data and the health provider inputs, such that the health provider inputs incorporate into the training network.

4. The system of claim 1, wherein the health provider user selects data of interest within the first and second subsets of extracted data at a health provider user interface to integrate with the AI.

5. The system of claim 1, wherein the health provider user comprises individuals or system entities including doctors, dentists, specialists, surgeons, nurses, physician assistants, dental assistants, alternative care providers, aestheticians, hospital systems, health-affiliated educational institutes and organizations, managed care living facilities, mental health organizations, or any combinations thereof.

6. The system of claim 1, wherein the health provider users of the social health network interact confidentially and communicate with one another regarding patient health, providing personalized health care, diagnosis, treatment, delivery of services, or any combinations thereof.

7. The system of claim 1, wherein the requested information includes the EHR of the patient user, and wherein the patient user owns the EHR and can authorize release of the EHR to the data analytics platform to share at a the second user interface used by the health provider user to support decision-making by one or more of the patient user or the health provider user.

8. The system of claim 1, wherein the patient user or the health provider user designates data of interest at the patient user interface and a health provider user interface, respectively, to select data and depict trends in data to analyze symptoms, diseases, treatments, care protocols, hospital services, effects and outcomes, or any combinations thereof, in view of a background, education, prior diagnoses and treatments, demographics, or geography of one or both of the patient user and the health provider user, or any combinations thereof, to support real-time decision making of the provider user.

9. The system of claim 1, wherein the customized depiction of data of conforms the training model to best practices in medicine and healthcare to improve treatment and care for patients.

10. The system of claim 1, wherein the patient user protects privacy and ownership of personalized health information by way of an alias and authenticates access through a verification process as to self-reporting of the patient user or by way of a health provider whom the patient authorizes to upload electronic health records of the patient user.

11. A computer implemented method comprising:

providing a system for management of healthcare to support a social network, the system comprising a data analytics platform that includes:

a patient controlled electronic health system comprising electronic health records (EHRs), the EHRs shared-with a plurality of health provider systems and external databases, each EHR having one or more patient records;

a computer-based infrastructure comprising one or more processors programmed to update profiles of patient users and provider users;

at least one database to centralize data, to collect and analyze patient data and health provider data, alone or in combination;

one or more servers to store the patient data and the health provider data, alone or in combination, the server (a) establishing social connections to create patient communities and (b) utilizing predictive analytics to support decision-making;

programming the server to:

create the patient user profile through a first electronic device and having access to a patient user interface, and create a provider user profile associated with the patient user profile and accessible via a provider user interface, wherein the EHRs requested from the patient are stored in a centralized database associated with the data analytics platform;

receive a request from a patient user of the social health network for information associated with the patient user at a first external system, wherein the information requested comprises information identifying the patient user and a health provider user associated with the patient user in the social health network;

determine if the first external system is authorized to transmit the information requested;

in response to a determination that the first external system is authorized to transmit the information requested, process the request and extract the patient record of the patient user from the first external system to provide extracted data;

transmit the extracted data directly to the social health network;

separate the extracted data into subsets, wherein a first subset comprises health information with the patient user identified and not available for sharing with a second external system, and a second subset comprises health information of the patient user available for sharing with the second external system when the patient user is de-identified;

de-identify a portion of the second subset of the extracted data to provide de-identified data of the patient user;

in response to a query from the second external system, perform data analytics using the extracted data including the de-identified data, wherein the step to de-identify occurs prior to the step to perform data analytics, thereby protecting privacy of the patient user; and access the database by way of the processor to predict deep learning models in personalized health comprising one or more of diagnosis, treatment, healthcare operations, administration and cost, or alternative healthcare solutions, wherein the one or more processors are programmed to implement a network learning model, the model generated from a training network that models data based on patient inputs, patient data from the patient record, or health provider data, wherein the patient profile is customized at the patient user interface by AI generated mathematical models of disease, condition, or treatment, and health provider user data matched to a patient user to create accurate knowledge graphs respective of the user and trending data graphs to generate recommendations to the patient user and provider user.

12. The method of claim 11, further comprising allowing the patient user to interconnect with a plurality of patient users through the patient user interface of the social health network.

13. The method of claim 11, further comprising providing the health provider user interface separate from the patient user interface to permit the health provider user access to the first subset of extracted data and to a plurality of health providers affiliated with the patient to access identifiable health information of the patient across health systems.

14. The method of claim 11, wherein the patient user authorizes the health provider user access to the second subset of the extracted data to permit the health provider user to interconnect with a plurality of health provider users not affiliated with the patient user to access data analytics of de-identified data.

15. The method of claim 11, wherein the patient user at the patient user interface selects data of interest from the extracted data and to depict trends in the selected data of interest to support decision-making of the patient user in real-time.

16. The method of claim 11, further comprising a health provider user interface wherein, through the provider user interface, the health provider user selects data of interest from the extracted data and depict trends in selected data of interest to support decision-making of the health provider user in real-time.

17. An electronic health network system comprising:
a patient controlled electronic health system comprising one or more health records, the health record shared-with a plurality of health provider systems and external databases;
one or more processors programmed to update profiles of patient users and provider users, wherein the profiles are optimized by a mathematical model;
at least one database to centralize data, to collect and analyze patient data and health provider data, alone or in combination;
one or more servers to store the patient data and the health provider data, alone or in combination, the server (a) establishing social connections to create patient communities and (b) utilizing predictive analytics to support decision-making in a data analytics platform;
the server programmed to:
create the patient user profile through a first electronic device and having access to a patient user interface, wherein the mathematical model creates a structured patient user interface that personalizes recommendations through knowledge graphs and data trends generated by artificial intelligence;
create the provider user profile associated with the patient user profile and accessible via a provider user interface, wherein the one or more health records requested from the patient are stored in a centralized database associated with the data analytics platform;
receive a request from a patient user of the social health network, for information associated with the patient user at a first external system, wherein the information requested comprises information identifying the patient user and a health provider user associated with the patient user;
determine if the first external system is authorized to transmit the information requested;
in response to a determination that the first external system is authorized to transmit the information requested, processing the request and extracting the patient record of the patient user from the first external system to provide extracted data;
transmit the extracted data directly to the social health network;
separate the extracted data into subsets, wherein a first subset comprises health information with the patient user identified and not available for sharing with a second external system, and a second subset comprises health
information of the patient user available for sharing with the second external system when the patient user is de-identified, wherein the second external system is different from the first external system;
de-identify a portion of the second subset of the extracted data to provide de-identified data of the patient user; and
in response to a query from the second external system, perform data analytics using the extracted data including the de-identified data,
wherein the step to de-identify occurs prior to the step to perform data analytics, thereby protecting privacy of the patient user, and
access the database by way of the processor to predict deep learning models in personalized health comprising one or more of—diagnosis, treatment, healthcare operations, administration and cost, and alternative healthcare solutions.

18. The system of claim 17, wherein the health provider users include global users across multiple disciplines.

19. The system of claim 17, wherein the one or more databases include designated levels for sharing of personalized health information, and the processor integrates predictive data analytics to optimize decision-making to support health diagnosis, treatment, and training of health provider users of the health network.

20. The system of claim 17, wherein the one or more databases are interconnected with servers to establish social connections among patient users and families of the health network, and to facilitate private communication of health information among health provider users in a confidential provider user interface of the health network sharing of data and data analytics.

21. The system of claim 17, wherein the method comprises creating the provider user profile while integrating provider demographics, experience data, provider clinical decisions and outcomes in real-time.

* * * * *